United States Patent
Liu

(10) Patent No.: US 10,712,454 B2
(45) Date of Patent: *Jul. 14, 2020

(54) X-RAY DETECTORS SUPPORTED ON A SUBSTRATE HAVING A METAL BARRIER

(71) Applicant: General Electric Company, Schenectady, NY (US)

(72) Inventor: Jie Jerry Liu, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 109 days.

This patent is subject to a terminal disclaimer.

(21) Appl. No.: 15/368,040

(22) Filed: Dec. 2, 2016

(65) Prior Publication Data

US 2017/0082558 A1 Mar. 23, 2017

Related U.S. Application Data

(63) Continuation-in-part of application No. 14/340,948, filed on Jul. 25, 2014, now Pat. No. 9,513,380.

(51) Int. Cl.

| G01T 1/20 | (2006.01) |
|---|---|
| G01T 1/24 | (2006.01) |
| G01N 23/04 | (2018.01) |
| H01L 27/30 | (2006.01) |
| H01L 51/00 | (2006.01) |
| H01L 51/44 | (2006.01) |

(Continued)

(52) U.S. Cl.
CPC .......... G01T 1/2018 (2013.01); A61B 6/4208 (2013.01); A61B 6/4233 (2013.01); G01N 23/04 (2013.01); G01T 1/202 (2013.01); G01T 1/24 (2013.01); H01L 27/308 (2013.01); H01L 51/0097 (2013.01); H01L 51/448 (2013.01); A61B 6/42 (2013.01); Y02E 10/549 (2013.01)

(58) Field of Classification Search
CPC ....... A61B 6/42; A61B 6/4233; A61B 6/4208; G01T 1/2018; G01T 1/24
USPC ..................................... 378/98.8; 250/370.09
See application file for complete search history.

(56) References Cited

U.S. PATENT DOCUMENTS 6,278,118 B1 * 8/2001 Homme ................ G01T 1/2018
                                                          250/367
6,594,339 B1    7/2003 Alving et al.
(Continued)

FOREIGN PATENT DOCUMENTS

| JP | 01267500 A | 10/1989 |
|---|---|---|
| JP | 2006078472 A | 3/2006 |

(Continued)

OTHER PUBLICATIONS

English translation of JP2013-029465 A, Japanese Platform for Patent Information (J-Plat Pat), translated on Aug. 27, 2019.*

(Continued)

Primary Examiner — Allen C. Ho

(57) ABSTRACT

An X-ray detector assembly includes a polymeric substrate having a lower surface and an upper surface, and an X-ray detector disposed on the upper surface of the polymeric substrate. The X-ray detector includes a thin-film-transistor array disposed on the substrate, an organic photodiode disposed on the thin-film-transistor array, and a scintillator disposed on the organic photodiode. A metal barrier extends substantially over the lower surface of the polymeric substrate.

14 Claims, 11 Drawing Sheets

(51) Int. Cl.
*A61B 6/00* (2006.01)
*G01T 1/202* (2006.01)

(56) References Cited

U.S. PATENT DOCUMENTS

| | | | |
|---|---|---|---|
| 6,642,524 B2* | 11/2003 | Vafi | G01T 1/2018 |
| | | | 250/370.09 |
| 6,743,524 B2 | 6/2004 | Schaepkens | |
| 6,825,473 B2* | 11/2004 | Watanabe | H01L 27/14676 |
| | | | 250/336.1 |
| 6,856,670 B2 | 2/2005 | Hoheisel | |
| 7,019,301 B2* | 3/2006 | Homme | G01T 1/2018 |
| | | | 250/366 |
| 7,034,306 B2 | 4/2006 | Homme et al. | |
| 7,067,817 B2* | 6/2006 | Suganuma | G01T 1/2928 |
| | | | 250/370.08 |
| 7,115,878 B2 | 10/2006 | Ikeda et al. | |
| 7,126,128 B2 | 10/2006 | Ikeda et al. | |
| 7,256,404 B2* | 8/2007 | Inoue | G01T 1/2018 |
| | | | 250/370.11 |
| 7,387,920 B2 | 6/2008 | Cho | |
| 7,402,814 B2 | 7/2008 | Vieux et al. | |
| 7,408,177 B2 | 8/2008 | Homme et al. | |
| 7,449,249 B2 | 11/2008 | Barbezat | |
| 7,453,065 B2* | 11/2008 | Saito | H01L 27/14601 |
| | | | 250/338.4 |
| 7,473,903 B2* | 1/2009 | DeJule | G01T 1/2018 |
| | | | 250/370.11 |
| 7,514,686 B2 | 4/2009 | Ogawa et al. | |
| 7,541,671 B2 | 6/2009 | Foust et al. | |
| 7,567,649 B1 | 7/2009 | Safai et al. | |
| 7,569,832 B2 | 8/2009 | Tredwell et al. | |
| 7,705,315 B2 | 4/2010 | Homme et al. | |
| 7,816,676 B2 | 10/2010 | Fourst et al. | |
| 7,847,258 B2* | 12/2010 | Yaegashi | G01T 1/2018 |
| | | | 250/370.08 |
| 7,956,332 B2 | 6/2011 | Bun-et al. | |
| 8,102,119 B2 | 1/2012 | Farquhar et al. | |
| 8,173,969 B2 | 5/2012 | Nishino et al. | |
| 8,236,424 B2 | 8/2012 | Schaepkens et al. | |
| 8,350,470 B2 | 1/2013 | Farquhar et al. | |
| 8,360,638 B2* | 1/2013 | Ohta | A61B 6/4283 |
| | | | 250/370.09 |
| 8,431,902 B2* | 4/2013 | Nakatsugawa | G01T 1/2018 |
| | | | 250/361 R |
| 8,497,481 B2 | 7/2013 | Shinba et al. | |
| 8,525,121 B2* | 9/2013 | Nakatsugawa | G01T 1/242 |
| | | | 250/367 |
| 8,532,262 B2* | 9/2013 | Iwakiri | A61B 6/4233 |
| | | | 250/370.09 |
| 8,541,751 B2* | 9/2013 | Nishino | G01T 1/243 |
| | | | 250/370.11 |
| 8,558,183 B2* | 10/2013 | Nakatsugawa | G01T 1/2018 |
| | | | 250/366 |
| 8,581,254 B2 | 11/2013 | Couture et al. | |
| 8,605,862 B2 | 12/2013 | Granfors et al. | |
| 8,618,491 B2* | 12/2013 | Shimizukawa | A61B 6/4233 |
| | | | 250/370.09 |
| 8,653,468 B2* | 2/2014 | Nakatsugawa | G21K 4/00 |
| | | | 250/370.09 |
| 8,704,184 B2* | 4/2014 | Iwakiri | G01T 1/2018 |
| | | | 250/361 R |
| 8,729,484 B2* | 5/2014 | Nishino | G01T 1/2018 |
| | | | 250/370.09 |
| 8,735,829 B2* | 5/2014 | Kuwabara | A61B 6/4233 |
| | | | 250/362 |
| 8,735,841 B2* | 5/2014 | Nakatsugawa | G01T 1/2018 |
| | | | 250/370.11 |
| 8,742,354 B2* | 6/2014 | Shimizukawa | G01T 1/16 |
| | | | 250/354.1 |
| 8,742,356 B2* | 6/2014 | Iwakiri | G01T 1/1644 |
| | | | 250/366 |
| 8,744,043 B2* | 6/2014 | Ohta | A61B 6/06 |
| | | | 378/62 |
| 8,779,369 B2* | 7/2014 | Ichimura | G21K 4/00 |
| | | | 250/369 |
| 8,791,420 B2* | 7/2014 | Nariyuki | G01T 1/20 |
| | | | 250/366 |
| 8,798,235 B2* | 8/2014 | Ohta | A61B 6/4494 |
| | | | 250/370.09 |
| 8,798,236 B2* | 8/2014 | Ohta | A61B 6/4494 |
| | | | 250/370.09 |
| 8,803,101 B2* | 8/2014 | Kaneko | A61B 6/4216 |
| | | | 250/370.09 |
| 8,829,455 B2* | 9/2014 | Nakatsugawa | A61B 6/4233 |
| | | | 250/370.09 |
| 8,841,628 B2* | 9/2014 | Kitano | H01L 27/14663 |
| | | | 250/393 |
| 8,853,808 B2* | 10/2014 | Homma | G01T 1/244 |
| | | | 257/428 |
| 8,861,680 B2* | 10/2014 | Iwakiri | G03B 42/04 |
| | | | 378/189 |
| 8,941,073 B2* | 1/2015 | Nabeta | G01T 1/2002 |
| | | | 250/370.11 |
| 8,970,755 B2* | 3/2015 | Nishino | H04N 5/32 |
| | | | 250/370.09 |
| 9,050,051 B2* | 6/2015 | Nakatsugawa | A61B 6/4233 |
| 9,063,239 B2* | 6/2015 | Oda | G01T 1/24 |
| 9,140,809 B2* | 9/2015 | Nakahashi | G01T 1/2018 |
| 9,168,016 B2* | 10/2015 | Ohta | G01T 1/24 |
| 9,176,239 B2* | 11/2015 | Kaneko | A61B 6/4216 |
| 9,182,504 B2* | 11/2015 | Nishino | G01T 1/2018 |
| 9,255,997 B2* | 2/2016 | Nakatsugawa | H01L 27/14618 |
| 9,257,480 B2* | 2/2016 | Zhao | H01L 27/14812 |
| 9,258,464 B2* | 2/2016 | Ohta | H04N 5/321 |
| 9,259,198 B2* | 2/2016 | Ohta | A61B 6/00 |
| 9,268,041 B2* | 2/2016 | Ohta | G01T 1/2018 |
| 9,285,489 B2 | 3/2016 | Couture et al. | |
| 9,335,422 B2* | 5/2016 | Oda | G01T 1/17 |
| 9,513,379 B2* | 12/2016 | Nishino | A61B 6/548 |
| 9,513,380 B2 | 12/2016 | Liu | |
| 9,515,276 B2* | 12/2016 | An | H01L 51/448 |
| 9,535,173 B2* | 1/2017 | Liu | G01N 23/04 |
| 9,581,702 B2* | 2/2017 | Van Arendonk | G01T 1/2002 |
| 9,662,086 B2* | 5/2017 | Ohta | A61B 5/0059 |
| 9,806,132 B2* | 10/2017 | An | G01T 1/2018 |
| 9,810,791 B2* | 11/2017 | Homma | G01T 1/2018 |
| 9,917,133 B2* | 3/2018 | Couture | G01T 1/2018 |
| 9,995,831 B2* | 6/2018 | Verschuren | G01T 1/2002 |
| 2006/0033032 A1 | 2/2006 | Inoue | |
| 2010/0072379 A1 | 3/2010 | Nishino | |
| 2012/0219114 A1 | 8/2012 | Iwakiri et al. | |
| 2012/0223240 A1 | 9/2012 | Ichimura et al. | |
| 2013/0026372 A1 | 1/2013 | Nabeta | |
| 2013/0037723 A1 | 2/2013 | Verschuren et al. | |
| 2015/0171134 A1 | 6/2015 | Couture et al. | |
| 2016/0027847 A1 | 1/2016 | Liu | |

FOREIGN PATENT DOCUMENTS

| | | |
|---|---|---|
| JP | 2010078415 A | 4/2010 |
| JP | 2013029465 A | 2/2013 |
| WO | 2016014637 | 1/2016 |

OTHER PUBLICATIONS

English translation of JP2010-078415 A, Japanese Platform for Patent Information (J-Plat Pat), translated on Aug. 27, 2019.*
English translation of JP2006-078472 A, Japanese Platform for Patent Information (J-Plat Pat), translated on Aug. 27, 2019.*
Iacchetti et al., "Multi-Layer Organic Squaraine-Based Photodiode for Indirect X-Ray Detection", Nuclear Science, IEEE Transactions on IEEE, Oct. 2012, pp. 1862-1867, vol. 59, Issue 5.
Gelinck et al., "X-Ray Imager Using Solution Processed Organic Transistor Arrays and Bulk Heterojunction Photodiodes on Thin Flexible Plastic Substrate", Organic Electronics, ScienceDirect, Oct. 2013, pp. 2602-2609, vol. 14, Issue 10.
Parthasarathy et al., Pending U.S. Appl. No. 13/955,355, entitled "Organic x-Ray Detector" filed Jul. 13, 2013, 22-pages.

(56) References Cited

OTHER PUBLICATIONS

Couture et al., Pending U.S. Appl. No. 14/014,003, entitled "Organic X-Rat Detector Assembly and Method of Manufacturing Same", filed Aug. 29, 2014, 41 pages.
Pending U.S. Appl. No. 14/144,253 entitled, "Method of Manufacturing Photodiode Detectors", filed Dec. 30, 2013, 27-pages.
Couture et al. Pending U.S. Appl. No. 14/103,989 entitled, "Optoelectronic Device With Flexible Substrate", filed Dec. 12, 2013, 12-pages.
Couture et al. Pending U.S. Appl. No. 14/109,454, entitled, "Method and System for Integrated Medical Transport Backboard Digital X-Ray Imaging Detector", filed Dec. 17, 2013, 21-pages.
PCT Search Report and Written Opinion issued in connection with corresponding PCT Application No. PCT/US2015/041488, which published as WO 2016014637, dated Nov. 3, 2015, 6-pages.
JP Patent Application No. 2017-504021, Notice of Preliminary Rejection dated May 7, 2019 [English Translation].

* cited by examiner

X-RAY DETECTORS SUPPORTED ON A SUBSTRATE HAVING A METAL BARRIER

CROSS-REFERENCE TO RELATED APPLICATION

This application is a continuation-in-part application of U.S. Ser. No. 14/340,948, filed Jul. 25, 2014, issued as U.S. Pat. No. 9,513,380 B2 on Dec. 6, 2016, entitled "X-Ray Detectors Supported On A Substrate Having A Surrounding Metal Barrier", the entire subject matter of which is incorporated herein by reference.

TECHNICAL FIELD

The present disclosure relates generally to X-ray detectors, and more particularly, to X-ray detectors supported on a substrate having a metal barrier.

BACKGROUND

X-ray radiation detectors include an electronically or optically active portion, e.g., radiation detector that is frequently disposed on a substrate. In those applications where a rigid electro-optical device is either preferable or acceptable, either glass or silicon is generally used as the substrate. In those applications where a flexible electro-optical device is desired, a polymeric film may serve as the substrate. However, moisture and oxygen diffuse rapidly through such polymeric film substrates, thereby causing the performance of the electro-optical devices disposed on the substrate to degrade or even fail. In addition, polymeric substrates are also subject to attack by chemicals used during processing of the electro-optical device.

U.S. Pat. No. 8,236,424 issued to Schaepkens et al. discloses an electro-optical device having at least one base and a multilayer coating surface disposed on at least one surface of the base. The at least one base may include either an optically or electronically active portion or a flexible polymeric material. The multilayer coating set includes at least one organic layer and at least one inorganic layer. The base and multilayer coating set are transparent to light in the visible portion of the spectrum. The inorganic layer may include at least one of silicon, a metal oxide, a metal nitride, and combinations thereof, and having a thickness of about 20 nanometers to about 200 nanometers. The multilayer coating set provides a barrier to moisture and oxygen and provides chemical resistance. The multilayer coating set is also mechanically flexible and thermally stable up to a glass transition temperature of the base.

There is a need for further X-ray detectors, and more particularly, to organic X-ray detectors supported on a substrate having a metal barrier.

SUMMARY

In an aspect of the present disclosure, an X-ray detector assembly includes a polymeric substrate having a lower surface and an upper surface, and an X-ray detector disposed on the upper surface of the substrate. The X-ray detector includes a thin-film-transistor array disposed on the substrate, an organic photodiode disposed on the thin-film-transistor array, and a scintillator disposed on the organic photodiode. A metal barrier extends substantially over an upper surface of the scintillator, substantially over peripherally-extending edges of the scintillator, the organic photodiode, and the thin-film-transistor array, and substantially over the lower surface of the substrate.

In another aspect of the present disclosure, an X-ray system includes the above-noted X-ray detector assembly, an X-ray source, and a controller operable for controlling the X-ray source and the X-ray detector.

In another aspect of the present disclosure, a method for fabricating an X-ray detector assembly includes providing a polymeric substrate having a lower surface and an upper surface, providing an X-ray detector disposed on the upper surface of the substrate, the X-ray detector includes a thin-film-transistor array, an organic photodiode, and a scintillator, and providing a metal barrier providing a barrier to oxygen and moisture extending substantially over an upper surface of the scintillator, substantially over peripherally-extending edges of the scintillator, the organic photodiode, and the thin-film-transistor array, and substantially over the lower surface of the substrate.

In an aspect of the present disclosure, an X-ray detector assembly includes a polymeric substrate having a lower surface and an upper surface, and an X-ray detector disposed on the upper surface of the substrate. The X-ray detector includes a thin-film-transistor array disposed on the substrate, an organic photodiode disposed on the thin-film-transistor array, and a scintillator disposed on the organic photodiode. A metal barrier extends substantially over the lower surface of the substrate.

In another aspect of the present disclosure, an X-ray system includes the above-noted X-ray detector assembly, an X-ray source, and a controller operable for controlling the X-ray source and the X-ray detector.

In another aspect of the present disclosure, a method for fabricating an X-ray detector assembly includes providing a polymeric substrate having a lower surface and an upper surface, providing an X-ray detector disposed on the upper surface of the substrate, the X-ray detector includes a thin-film-transistor array, an organic photodiode, and a scintillator, and providing a metal barrier providing a barrier to oxygen and moisture extending substantially over the lower surface of the substrate.

DRAWINGS

The foregoing and other features, aspects and advantages of this disclosure will become apparent from the following detailed description of the various aspects of the disclosure taken in conjunction with the accompanying drawings, wherein.

DETAILED DESCRIPTION

As described in greater detail below, the present disclosure is directed to X-ray detectors employing a surrounding metal barrier layer that may improve X-ray detector reliability. For example, the metal barrier layer may form a seal or barrier to oxygen and moisture for protecting the components of the X-ray detector and the supporting substrate. Such a technique may be desirable for mechanically flexible X-ray detectors having a polymeric or plastic substrate. The metal barrier may be a solid metal coating or a metal foil such as including substantially one or more elemental metals, and substantially not include oxides.

Each embodiment presented below facilitates the explanation of certain aspects of the disclosure, and should not be interpreted as limiting the scope of the disclosure. Moreover, approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value. When introducing elements of various embodiments, the articles "a," "an," "the," and "said" are intended to mean that there are one or more of the elements. The terms "comprising," "including," and "having" are intended to be inclusive and mean that there may be additional elements other than the listed elements. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. Any examples of operating parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

Figure 1:
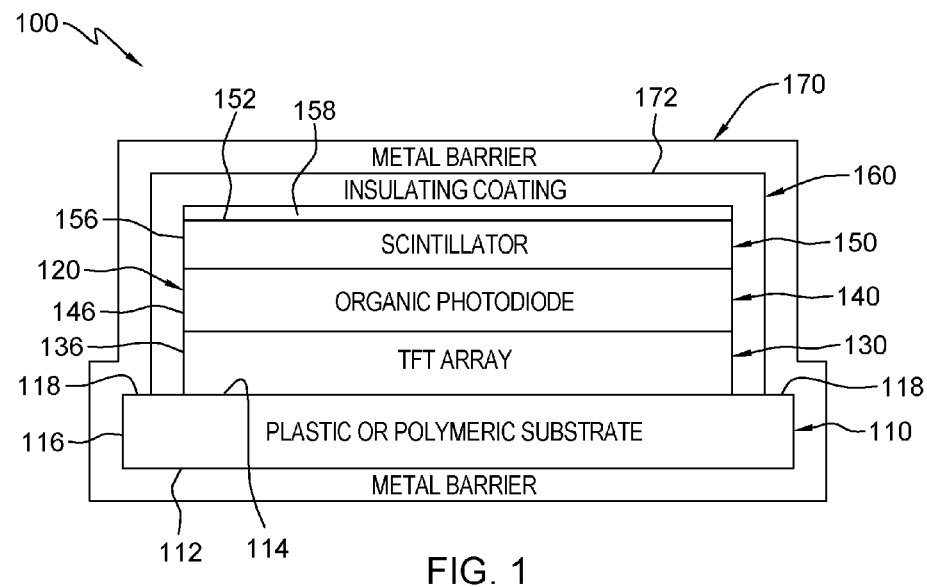
FIG. 1 is a cross-sectional view of one embodiment of an X-ray detector assembly in accordance with aspects of the present disclosure.

FIG. 1 illustrates one embodiment of an X-ray detector assembly 100 in accordance with aspects of the present disclosure. In this illustrated embodiment, X-ray detector assembly 100 may employ a metal material or barrier 170 substantially surrounding an X-ray detector 120. For example, X-ray detector assembly 100 may include a plastic or polymeric substrate 110, X-ray detector 120 having, for example, a TFT (thin-film-transistor) array 130 disposed on the polymeric substrate 110, an organic photodiode 140 disposed on the TFT array 130, a scintillator 150 disposed on the organic photodiode 140, and a metal material or barrier 170 such as a metal coating disposed around X-ray detector 120 supported on polymeric substrate 110.

Polymeric substrate 110 may include a lower surface 112, an upper surface 114, and a peripherally-extending edge 116. TFT array 130 may be disposed on the upper surface 114 of the polymeric substrate 110. TFT array 130 may include a peripherally-extending edge 136, organic photodiode 140 may include a peripherally-extending edge 146, and scintillator 150 may include a peripherally-extending edge 156.

Metal barrier 170 may extend substantially over an upper surface 152 and peripherally-extending edge 156 of scintillator 150, peripherally-extending edge 146 of organic photodiode 140, peripherally-extending edge 136 of TFT array 130, and lower surface 112. For example, the metal barrier 170 may be a continuous one-piece or monolithic metal barrier disposed entirely around the X-ray detector 120 supported on the substrate 110.

An insulating layer 160 may extend between an inner surface 172 of metal barrier 170 and X-ray detector 120. In this illustrated embodiment, insulating layer 160 may be sandwiched between inner surface 172 of metal barrier 170 and upper surface 152 and peripherally-extending edge 156 of scintillator 150, peripherally-extending edge 146 of organic photodiode 140, and peripherally-extending edge 136 of TFT array 130. The insulating layer 160 may electrically insulate metal barrier 170 from the components of the X-ray detector 120. A reflective layer 158 may be disposed between scintillator 150 and insulating layer 160. The lower surface of the reflective layer 158 aids in reflecting light downwardly towards the organic photodiode 140 for increasing the absorption of light by the organic photodiode 140.

It will be appreciated that in X-ray detectors where the peripherally-extending edges of the TFT array 130, organic photodiode 140, and scintillator 150 do not align with each other, the metal barrier 170 and/or insulating layer 160 may extend over peripherally-extending portions of the lower and/or upper surfaces of the TFT array 130, organic photodiode 140, and/or scintillator 150. For example, as shown in FIG. 1, plastic substrate 110 may include a peripherally extending upper edge portion 118 which extends past the peripherally-extending edges 136 of TFT array 130. Metal barrier 170 may extend over a peripherally-extending upper edge portion 118 of polymer substrate 110.

As described above, metal barrier 170 may provide a seal substantially extending around X-ray detector 120 and polymeric substrate 110. In this illustrated embodiment, metal barrier 170 may completely and continuously extend around X-ray detector 120 and polymeric substrate 110. Metal barrier 170 may provide a generally hermetic or airtight seal or closure around X-ray detector 120 and polymeric substrate 110 that acts as a barrier to prevent the exposure of the X-ray detector 120 and polymeric substrate 110 to moisture, oxygen, and/or other gases. Metal barrier 170 may also act as a barrier to chemical attack of the X-ray detector 120 and polymeric substrate 110. Suitable methods for applying the metal barrier 170 or coating may include, but not limited to, physical vapor deposition (PVD), thermal evaporation, sputtering, eBeam, etc.

Figure 2:
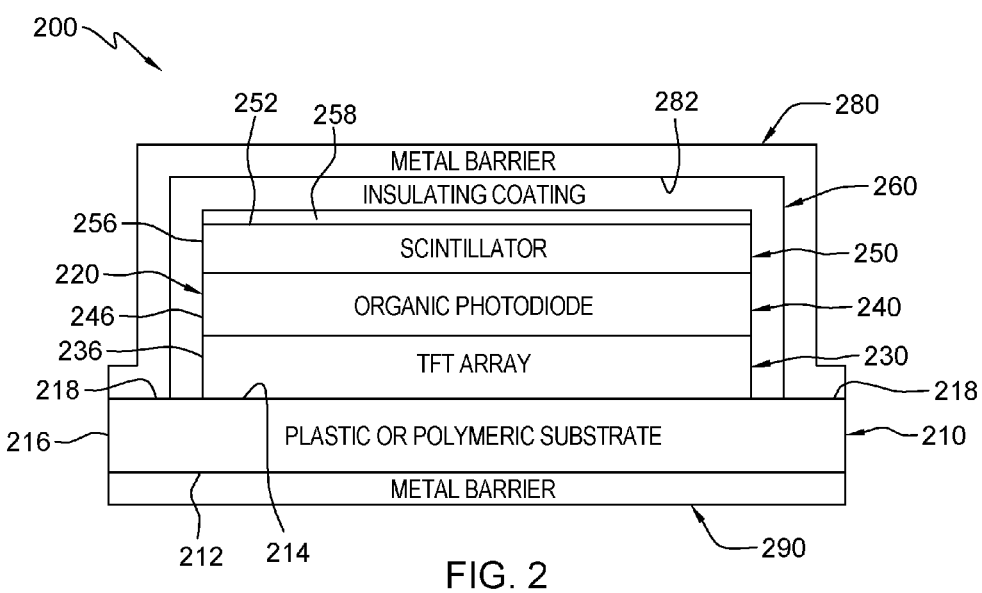
FIG. 2 is a cross-sectional view of another embodiment of an X-ray detector assembly in accordance with aspects of the present disclosure.

FIG. 2 illustrates another embodiment of an X-ray detector assembly 200 in accordance with aspects of the present disclosure. In this illustrated embodiment, X-ray detector assembly 200 may employ a metal barrier 280 and 290 substantially surrounding an X-ray detector. For example, X-ray detector assembly 200 may include a plastic or polymeric substrate 210, an X-ray detector 220 having, for example, a TFT (thin-film-transistor) array 230 disposed on the polymeric substrate 210, an organic photodiode 240 disposed on the TFT array 230, a scintillator 250 disposed on the organic photodiode 240, and metal material or barriers 280 and 290 such as a metal coating disposed around X-ray detector 220 supported on polymeric substrate 210. As described below, metal barrier 280 may be disposed over the X-ray detector 220, and metal barrier 290 may be disposed over the polymeric substrate 210.

Polymeric substrate 210 may include a lower surface 212, an upper surface 214, and a peripherally-extending edge 216. TFT array 230 may be disposed on the upper surface 214 of the polymeric substrate 210. TFT array 230 may include a peripherally-extending edge 236, organic photodiode 240 may include a peripherally-extending edge 246, and scintillator 250 may include a peripherally-extending edge 256.

Metal barrier 280 may extend substantially over an upper surface 252 and peripherally-extending edge 256 of scintillator 250, peripherally-extending edge 246 of organic photodiode 240, and peripherally-extending edge 236 of TFT array 230. Metal barrier 290 may extend substantially over a lower surface 212 of polymeric substrate 210.

An insulating layer 260 may extend between an inner surface 282 of metal barrier 280 and X-ray detector 220. In this illustrated embodiment, insulating layer 260 may be sandwiched between inner surface 282 of metal barrier 280 and upper surface 252 and peripherally-extending edge 256 of scintillator 250, peripherally-extending edge 246 of organic photodiode 240, and peripherally-extending edge 236 of TFT array 230. The insulating layer 260 may electrically insulate metal barrier 280 from the components of the X-ray detector 220. A reflective layer 258 may be disposed between scintillator 250 and insulating layer 260. The lower surface of the reflective layer aids in reflecting light downwardly towards the organic photodiode 240 for increasing the absorption of light by the organic photodiode 240.

It will be appreciated that in X-ray detectors where the peripherally-extending edges of the TFT array 230, organic photodiode 240, and scintillator 250 do not align with each other, the metal barrier 280 and 290 and/or insulating layer 260 may extend over peripherally-extending portions of the lower and/or upper surfaces of the TFT array 230, organic photodiode 240, and/or scintillator 250. As shown in FIG. 2, polymeric substrate 210 may include a peripherally extending portion which extends past the peripherally-extending edges of TFT array 230. Metal barrier 280 may extend over a peripherally-extending upper edge portion 218 of polymer substrate 210. For example, in this illustrated embodiment, peripherally-extending edge portions of the polymer substrate 210 may be sandwiched between the peripheral-extending edge portions of metal barriers 280 and 290.

Metal barriers 280 and 290 may provide a seal substantially extending around X-ray detector 220 and polymeric substrate 210. In this illustrated embodiment, metal barrier 280 may completely and continuously extend over upper surfaces and side surfaces of X-ray detector 220. Metal barrier 290 may extend substantially over the lower surface 212 of polymeric substrate 210. Metal barriers 280 and 290 may provide a generally hermetic or airtight seal or closure around X-ray detector 220 and upper surface 214 and lower surface 212 of polymeric substrate 210 that acts as a barrier to prevent the exposure of the X-ray detector 220 and polymeric substrate 210 to moisture, oxygen, and/or other gases. Metal barriers 280 and 290 may also act as a barrier to chemical attack of the X-ray detector 220 and polymeric substrate 210. Suitable methods for applying the metal barriers or coatings may include, but not limited to, physical vapor deposition (PVD), thermal evaporation, sputtering, eBeam, etc.

Figure 3:
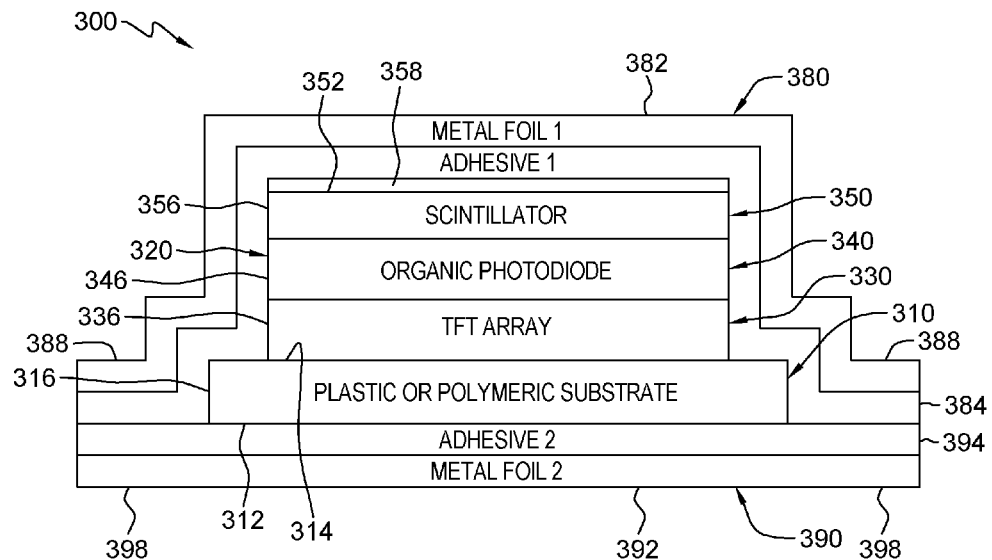
FIG. 3 is a cross-sectional view of another embodiment of an X-ray detector assembly in accordance with aspects of the present disclosure.

FIG. 3 illustrates another embodiment of an X-ray detector assembly 300 in accordance with aspects of the present disclosure. In this illustrated embodiment, X-ray detector system 300 may employ a metal barrier substantially surrounding an X-ray detector 320. For example, X-ray detector assembly 300 may include a plastic or polymeric substrate 310, an X-ray detector 320 having, for example, a TFT (thin-film-transistor) array 330 disposed on the polymeric substrate 310, an organic photodiode 340 disposed on the TFT array 330, a scintillator 350 disposed on the organic photodiode 340, and a metal material or barrier such as adhesively-backed metal foils 380 and 390 disposed substantially around X-ray detector 320 supported on polymeric substrate 310. For example, adhesively-backed metal foils 380 and 390 may include metal foil 382 and 392 having attached to one side of the metal foil adhesive layers 384 and 394, respectively.

In this illustrated embodiment, plastic substrate 321 may include a lower surface 312, an upper surface 314, and a peripherally-extending edge 316. TFT array 330 may be disposed on the upper surface 314 of the plastic substrate 310. TFT array 330 may include a peripherally-extending edge 336, organic photodiode 340 may include a peripherally-extending edge 346, and scintillator 350 may include a peripherally-extending edge 356. The adhesively-backed metal foils may be disposed on and removable from a roll. Alternatively, the adhesively-backed metal foils may be disposed in a sheet form having a releasably attached release sheet (not shown) for protecting the adhesive layer until removal of the release sheet. In still other embodiment, a spray of adhesive may be applied to a surface of the foils. The adhesive layer may act as an insulating layer that extends between the metal foil and the X-ray detector 320 to electrically insulate the metal foil from the components of the X-ray detector 320. A reflective layer 358 may be disposed between scintillator 350 and adhesive layer 384. The lower surface of the reflective layer 358 aids in reflecting light downwardly towards the organic photodiode 340 for increasing the absorption of light by the organic photodiode 340.

In this illustrated embodiment shown in FIG. 3, adhesively-backed metal foil 380 may be draped substantially over and attached to an upper surface 352 of scintillator 350 and draped substantially over or confirm to the peripherally-extending edges of the X-ray detector 320. Adhesively-backed metal foil 390 may be attached substantially over lower surface 312 of polymeric substrate 310. A peripherally-extending portion 388 of adhesively-backed metal foil 380 may extend outwardly from the peripherally-extending side edge of the X-ray detector 320 and the peripherally-extending side edge of the polymeric substrate 310, and a peripherally-extending portion 398 of adhesively-backed metal foil 390 may extend outwardly from the peripherally-extending side edge of the polymeric substrate 310. Peripherally-extending portion 388 of foil 380 may be adhesively attached to peripherally-extending portion 398 of foil 390.

In other embodiments, a single adhesively-backed metal foil may be employed for substantially covering the X-ray detector assembly 300. For example, a single adhesively-backed metal foil may be operably sized so that a first portion may be adhered to the bottom of the polymeric substrate 310 and a second portion folded around one side of the X-ray detector 320, across the top of the scintillator 350, and over the other side of the X-ray detector 320, with a portion of the second portion adhesively attaching to the first portion.

In still other embodiments, an adhesive may be applied to the back of the metal foil or to the outer surfaces of the X-ray detector 320 and lower surface 312 of the polymeric substrate 310 prior to securing the metal foil or foils. In other embodiments, a first foil may be disposed on the lower surface 312 of the polymeric substrate 310, the X-ray detector 320 fabricated on the upper surface 314 of the polymeric substrate 310, and then a second foil disposed over the X-ray detector 320.

Metal foils 380 and 390 may provide a seal substantially extending around X-ray detector 320 and polymeric substrate 310. In this illustrated embodiment, metal foil 380 may completely and continuously extend over an upper surface and side surfaces of X-ray detector 320. Metal foil 390 may extend over the lower surface 312 of polymer substrate 310. Metal foils 380 and 390 may provide a generally hermetic or airtight seal or closure around X-ray detector 320 and upper surface 314 and lower surface 312 of polymeric substrate 310 that acts as a barrier to prevent the exposure of the X-ray detector 320 and polymeric substrate 310 to moisture, oxygen, and/or other gases. Metal foils 380 and 390 may also act as a barrier to chemical attack of the X-ray detector 320 and polymeric substrate 310.

Figure 4:
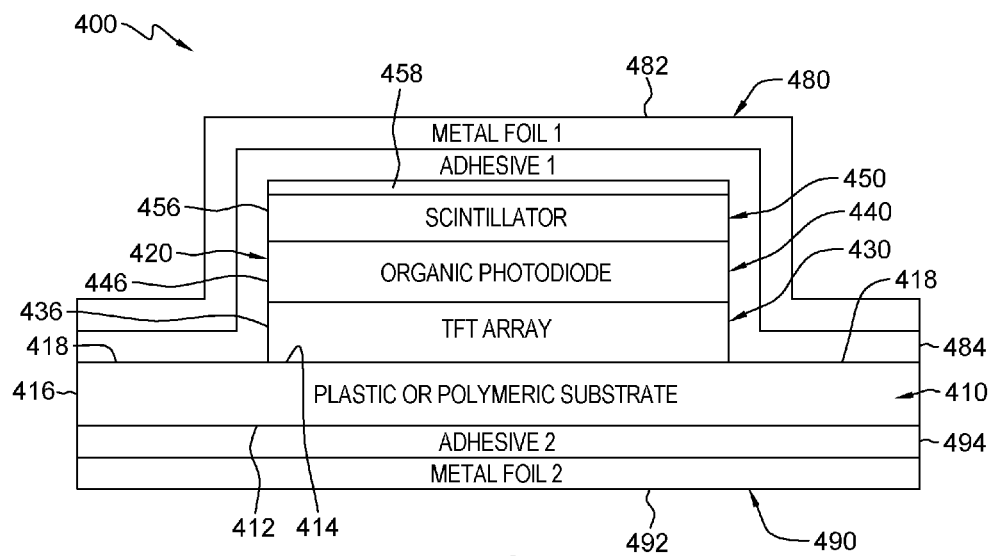
FIG. 4 is a cross-sectional view of another embodiment of an X-ray detector assembly in accordance with aspects of the present disclosure.

FIG. 4 illustrates another embodiment of an X-ray detector assembly 400 in accordance with aspects of the present disclosure. In this illustrated embodiment, X-ray detector assembly 400 may employ a metal foil for substantially surrounding an X-ray detector assembly. For example, X-ray detector assembly 400 may include a plastic or polymeric substrate 410, an X-ray detector 420 having, for example, a TFT (thin-film-transistor) array 430 disposed on the polymeric substrate, an organic photodiode 440 disposed on the TFT array, a scintillator 450 disposed on the organic photodiode, and a metal material or barrier such as an adhesively-backed metal foils 480 and 490 disposed substantially around X-ray detector 420 supported on polymeric substrate 410. For example, the adhesively-backed metal foils 480 and 490 may include metal foil 482 and 492 having attached to one side of the metal foil adhesive layers 484 and 494, respectively.

In this illustrated embodiment, plastic substrate 420 may include a lower surface 412, an upper surface 414, and a peripherally-extending edge 416. TFT array 430 may be disposed on the upper surface of the plastic substrate. TFT array 430 may include a peripherally-extending edge 436, organic photodiode 440 may include a peripherally-extending edge 446, and scintillator 450 may include a peripherally-extending edge 456. The adhesively-backed metal foils may be disposed on and removable from a roll. Alternatively, the adhesively-backed metal foils may be disposed in a sheet form having a releasably attached release sheet (not shown) for protecting the adhesive layer until removal of the release sheet. In still other embodiment, a spray of adhesive may be applied to a surface of the foils. The adhesive layer may act as an insulating layer that extends between the metal foil and the X-ray detector to electrically insulate the metal foil from the components of the X-ray detector. A reflective layer 458 may be disposed between scintillator 450 and adhesive layer 484. The lower surface of the reflective layer aids in reflecting light downwardly towards the photodetector for increasing the absorption of light by the photodetector.

In this illustrated embodiment shown in FIG. 4, adhesively-backed metal foil 480 may be draped substantially over and attached to an upper surface 452 of scintillator 450, draped substantially over or confirm to and attached to the peripherally-extending sides of the X-ray detector 420, and attached to a peripherally-extending upper edge portion 418 of polymer substrate 410. Adhesively-backed metal foil 490 may be disposed substantially over lower surface 412 of substrate 410. For example, in this illustrated embodiment, peripherally-extending edge portions of the polymer substrate may be sandwiched between the peripheral-extending edge portions of metal foils 480 and 490.

In still other embodiments, an adhesive may be applied to the back of the metal foil or to the outer surfaces of the X-ray detector and lower surfaces of the substrate prior to securing the metal foil or foils. In other embodiments, a first foil may be disposed on the bottom surface of the substrate, the X-ray detectors fabricated on top of the substrate, and then a second foil disposed over the X-ray detector.

Metal foils 480 and 490 may provide a seal substantially extending around X-ray detector 420 and polymeric substrate 410. In this illustrated embodiment, metal foils 480 may completely and continuously extend over an upper surface and side surfaces of X-ray detector 420. Metal foils 490 may extend over the lower surface of polymer substrate 410. Metal foils 480 and 490 may provide a generally hermetic or airtight seal or closure around X-ray detector 420 and upper and lower surfaces of polymeric substrate 410 that acts as a barrier to prevent the exposure of the X-ray detector and polymeric substrate to moisture, oxygen, and/or other gases. Metal foils 480 and 490 may also act as a barrier to chemical attack of the X-ray detector and polymeric substrate.

Figure 5:
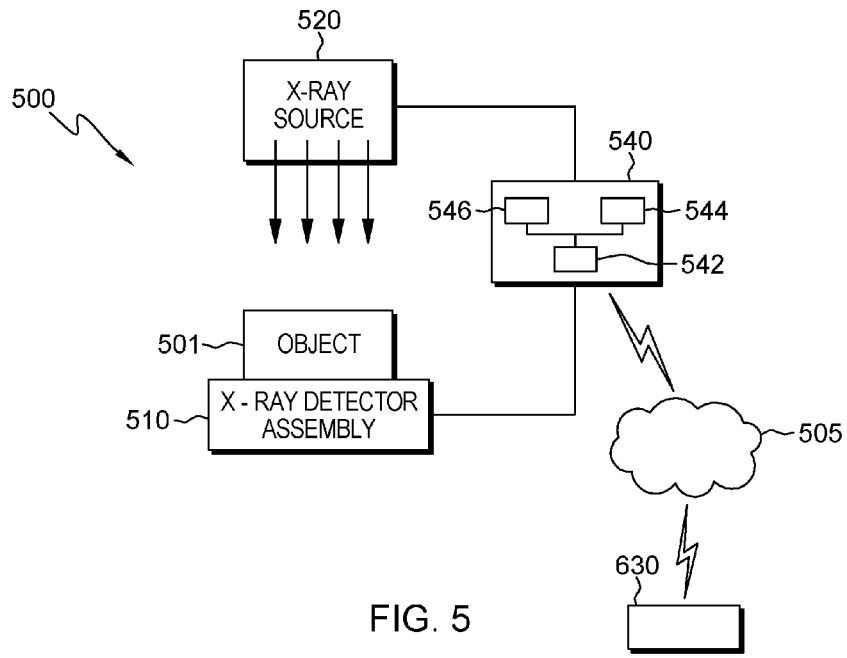
FIG. 5 is a block diagram of one embodiment of an X-ray detector system in accordance with aspects of the present disclosure.

FIG. 5 illustrates a block diagram of an X-ray detector system 500 for imaging an object 501 in accordance with aspects of the present disclosure. For example, X-ray detector system 500 may include an X-ray detector assembly 510, such as the techniques disclosed in X-ray detector assemblies 100 (FIG. 1), 200 (FIG. 2), 300 (FIG. 3), and 400 (FIG. 4), an X-ray source 520, and a computing unit 540. The X-ray source 520 may be, for example, an X-ray tube, and the computing unit 540 may include, for example, a processor or a microcontroller 542, one or more memory devices 544, and one or more input and/or output devices 546. The computing unit 540 may be operable for transmitting to and receiving from a remote computing unit 630 such as via a communications network 505. The communications network 505 may be a global communications network such as the Internet, or a local area network, or other suitable network. Computing unit 540 and/or remote computing unit 630 may be operable for controlling the X-ray source 520 and the X-ray detector assembly 510 for obtaining images, and/or for processing the obtained images. While the illustrated X-ray detector assembly 510 is illustrated as being flat in FIG. 5, it will be appreciated that the X-ray detector assembly 510 may be a non-flat, such as a curved or flexible X-ray detector assembly.

Figure 6:
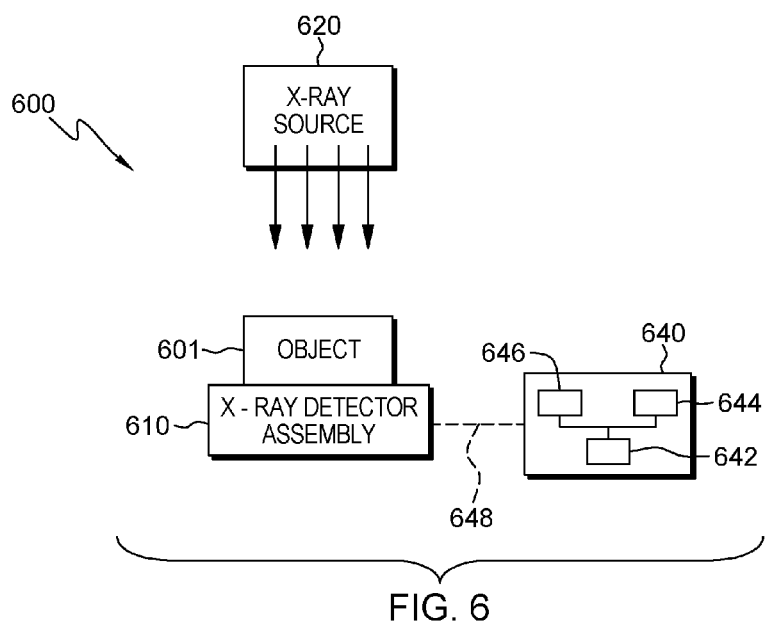
FIG. 6 is a block diagram of another embodiment of an X-ray detector system in accordance with aspects of the present disclosure.

FIG. 6 illustrates a block diagram of an X-ray detector system 600 for imaging an object 601 in accordance with aspects of the present disclosure. For example, X-ray detector system 600 may include an X-ray detector assembly 610, such as the techniques disclosed in X-ray detector assemblies 100 (FIG. 1), 200 (FIG. 2), 300 (FIG. 3), and 400 (FIG. 4), an X-ray source 620, and a computing unit 640. The X-ray source 620 may be, for example, an X-ray tube, and the computing unit 640 may include, for example, a processor or a microcontroller 642, one or more memory devices 644, and one or more input and/or output devices 646. Computing unit 640 may be operably connected to the X-ray detector assembly 610 such as by a wire or a wireless connection 648, e.g., WiFi, for transmitting to and receiving signals and/or data from X-ray detector assembly 610 and/or X-ray source 620. Computing unit 640 may be operable for controlling the X-ray source 620 and the X-ray detector assembly 610 for obtaining images, and/or for processing the obtained images. While the illustrated X-ray detector assembly 610 is illustrated as being flat in FIG. 6, it will be appreciated that the X-ray detector assembly 610 may be non-flat such as a curved or flexible X-ray detector assembly.

Figure 7:
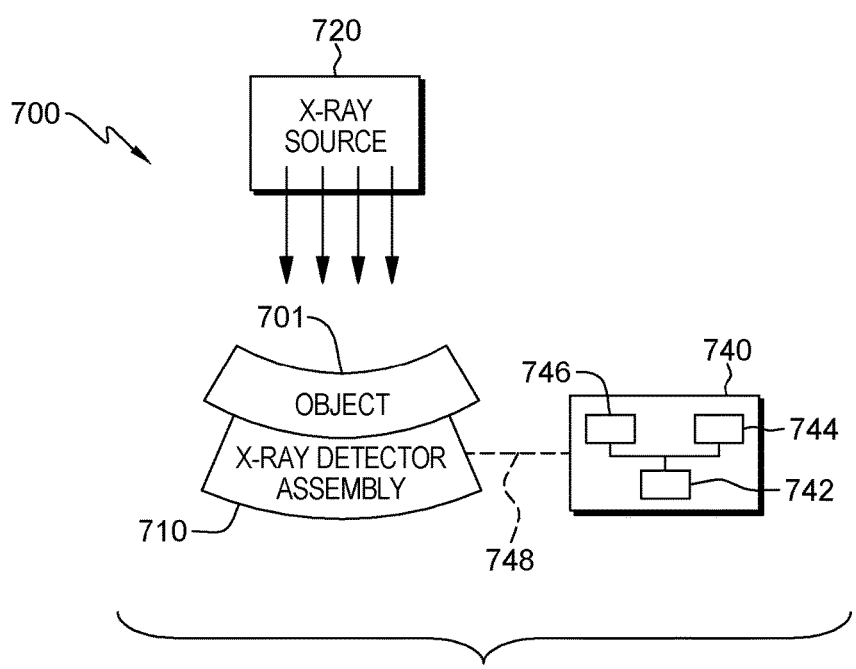
FIG. 7 is a block diagram of another embodiment of an X-ray detector system in accordance with aspects of the present disclosure.

FIG. 7 illustrates a block diagram of an X-ray detector system 700 for imaging an object 701 in accordance with aspects of the present disclosure. For example, X-ray detector system 700 may include an X-ray detector assembly 710, such as X-ray detector assembly employing the techniques disclosed in the X-ray detector assemblies 100 (FIG. 1), 200 (FIG. 2), 300 (FIG. 3), and 400 (FIG. 4), an X-ray source 720, and a computing unit 740. The X-ray source 720 may be, for example, an X-ray tube, and the computing unit 740 may include, for example, a processor or a microcontroller 742, one or more memory devices 744, and one or more input and/or output devices 746. Computing unit 740 may be operably connected to the X-ray detector assembly 710 such as by a wire or a wireless connection 748, e.g., WiFi, for transmitting to and receiving signals and/or data from X-ray detector assembly 710 and/or X-ray source 720. Computing unit 740 may be operable for controlling the X-ray source 720 and the X-ray detector assembly 710 for obtaining images, and/or for processing the obtained images. While the illustrated X-ray detector assembly 710 is illustrated as being curved in FIG. 7, it will be appreciated that the X-ray detector assembly 710 may be a flexible X-ray detector assembly.

In operation, the scintillator converts X-ray photons incident on its surface to optical photons. The optical photons may then be converted to electrical signals by the photodiode. The electrical charges may be stored and read out from storage in the TFT array. These electrical signals are acquired and processed to construct an image of the features (e.g., anatomy, pipe, or other structure) within a target.

Figure 8:
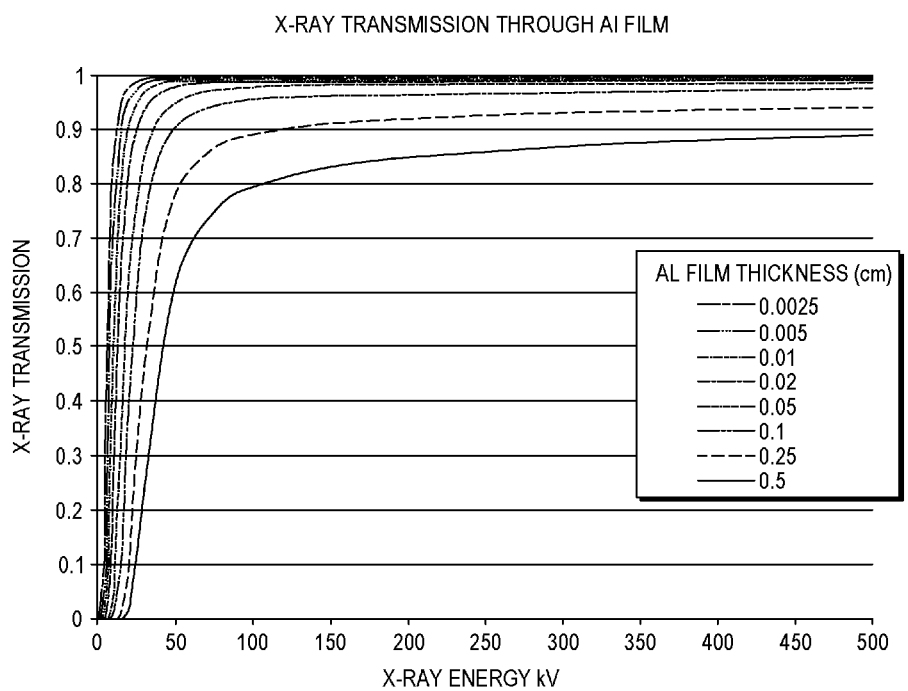
FIG. 8 is a graph of X-ray transmission though various thicknesses of aluminum verses X-ray energy.

The selection of the metal material and the thickness may be adjusted depending on the X-ray source, and the metal material's characteristic absorption coefficient. For instance, as shown in FIG. 8, over 98-percent X-ray transmission may be achieved with about 0.02 centimeter or less of an aluminum coating for about a 70 kV X-ray source, typically used in medical applications, or about 0.1 centimeter or less of an aluminum coating for about a 400 kV X-ray source, typically used for industrial inspection applications.

Figure 9:
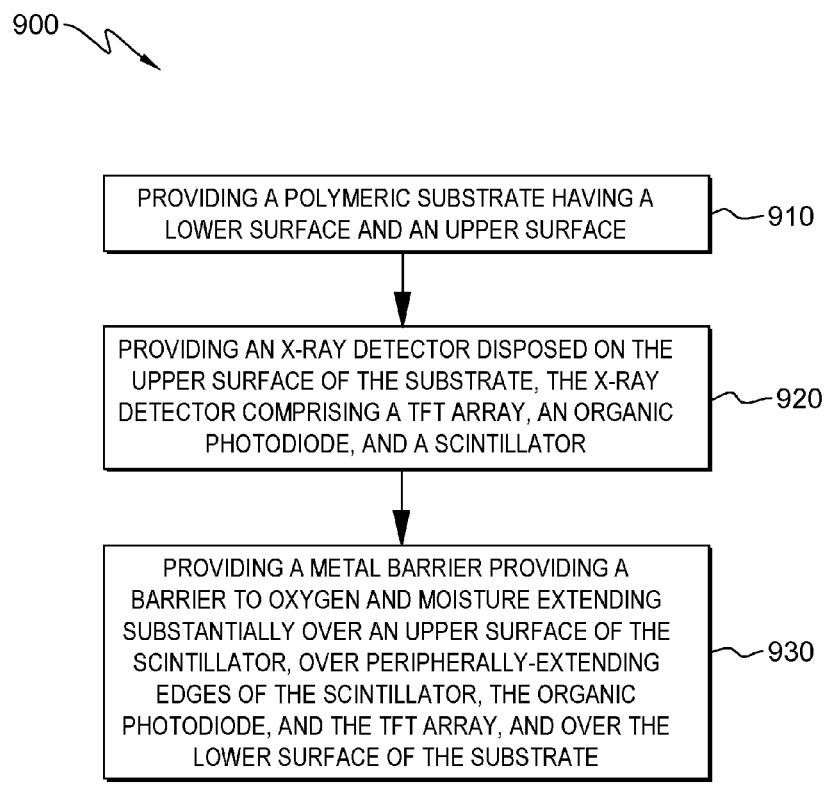
FIG. 9 is a flowchart of one embodiment of a method for forming an organic X-ray detector in accordance with aspects of the present disclosure.

FIG. 9 illustrates one embodiment of a method 900 for fabricating an X-ray detector assembly. In this exemplary embodiment, method 900 may include at 910, providing a polymeric substrate having a lower surface and an upper surface, and at 920, providing an X-ray detector disposed on the upper surface of the polymeric substrate. The X-ray detector includes a TFT (thin-film-transistor) array, an organic photodiode, and a scintillator. At 930, a metal barrier is provided providing a barrier to oxygen and moisture extending substantially over an upper surface of the scintillator, substantially over peripherally-extending edges of the scintillator, the organic photodiode, and the TFT array, and over the lower surface of the polymeric substrate.

As described in greater detail below, the present disclosure is directed to X-ray detectors employing a metal barrier layer that may improve X-ray detector reliability. For example, the metal barrier layer may form a seal or barrier to oxygen and moisture for protecting the supporting substrate. Such a technique may be desirable for mechanically flexible X-ray detectors having a polymeric or plastic substrate. The metal barrier may be a solid metal coating or a metal foil such as including substantially one or more elemental metals, and substantially not include oxides.

Figure 10:
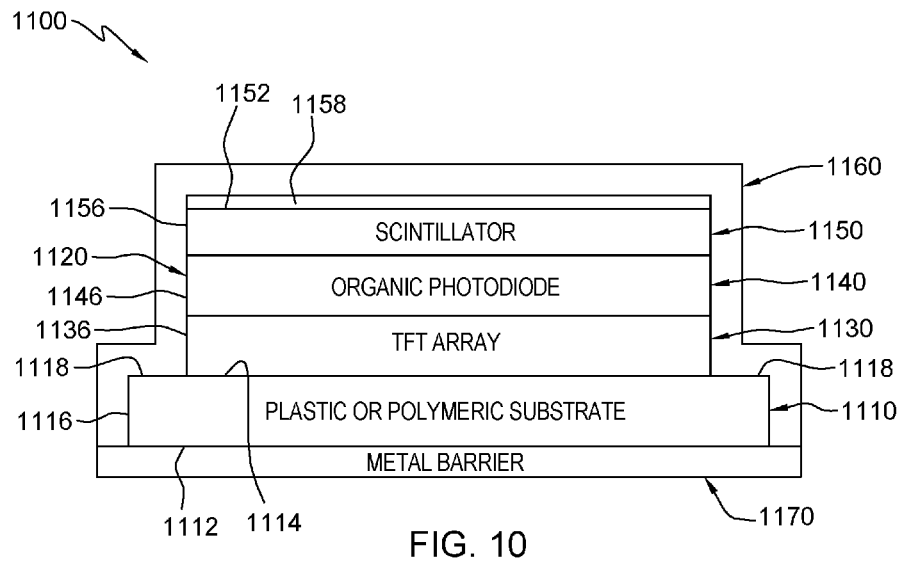
FIG. 10 is a cross-sectional view of another embodiment of an X-ray detector assembly in accordance with aspects of the present disclosure.

FIG. 10 illustrates an embodiment of an X-ray detector assembly 1100 in accordance with aspects of the present disclosure. In this illustrated embodiment, X-ray detector assembly 1100 may employ a metal material or barrier 1170 and a sealing layer 1160 that substantially surrounds an X-ray detector 1120. For example, X-ray detector assembly 1100 may include a plastic or polymeric substrate 1110, X-ray detector 1120 having, for example, a TFT (thin-film-transistor) array 1130 disposed on the polymeric substrate 1110, an organic photodiode 1140 disposed on the TFT array 1130, a scintillator 1150 disposed on the organic photodiode 1140, and metal barrier 1170 such as a metal coating disposed on a portion of polymeric substrate 1110.

Polymeric substrate 1110 may include a lower surface 1112, an upper surface 1114, and a peripherally-extending edge 1116. TFT array 1130 may be disposed on the upper surface 1114 of the polymeric substrate 1110. TFT array 1130 may include a peripherally-extending edge 1136, organic photodiode 1140 may include a peripherally-extending edge 1146, and scintillator 1150 may include a peripherally-extending edge 1156.

Metal barrier 1170 may extend substantially over lower surface 1112 of polymeric substrate 1110. In some embodiments, the metal barrier 1170 may be a continuous one-piece or monolithic metal barrier disposed entirely on the lower surface 1112 of polymeric substrate 1110.

A sealing layer 1160 may extend over X-ray detector 1120. In this illustrated embodiment, sealing layer 1160 may extend over upper surface 1152 and peripherally-extending edge 1156 of scintillator 1150, peripherally-extending edge 1146 of organic photodiode 1140, and peripherally-extending edge 1136 of TFT array 1130. A reflective layer 1158 may be disposed between scintillator 1150 and sealing layer

1160. The lower surface of the reflective layer 1158 aids in reflecting light downwardly towards the organic photodiode 1140 for increasing the absorption of light by the organic photodiode 1140. Sealing layer 1160 may be a polymer sealant such as an epoxy sealant, or other suitable sealing material.

It will be appreciated that in X-ray detectors where the peripherally-extending edges of the TFT array 1130, organic photodiode 1140, and scintillator 1150 do not align with each other, the sealing layer 1160 may extend over peripherally-extending portions of the lower and/or upper surfaces of the TFT array 1130, organic photodiode 1140, and/or scintillator 1150. For example, as shown in FIG. 10, polymeric substrate 1110 may include a peripherally extending upper edge portion 1118 which extends past the peripherally-extending edges 1136 of TFT array 1130.

As described above, metal barrier 1170 may provide a seal substantially extending below X-ray detector 1120 and on and in contact with the bottom of polymeric substrate 1110. In this illustrated embodiment, metal barrier 1170 may completely and continuously extend along the bottom of polymeric substrate 1110. Metal barrier 1170 may provide a generally hermetic or airtight seal along the bottom of polymeric substrate 1110 that acts as a barrier to prevent the exposure of polymeric substrate 1110 to moisture, oxygen, and/or other gases. Metal barrier 1170 may also act as a barrier to chemical attack of the X-ray detector 1120 and polymeric substrate 1110. Suitable methods for applying the metal barrier 1170 or coating may include, but not limited to, physical vapor deposition (PVD), thermal evaporation, sputtering, eBeam, etc.

As shown in FIG. 10, sealing layer 1160 may be applied onto X-ray detector 1120 and peripheral edges 1116 of polymer substrate 1110, and then metal barrier 1170 may be applied to bottom surface 1112 of polymeric substrate 1110. In other embodiments, a metal barrier may be applied to the bottom of the polymeric substrate, and then a sealing layer or structure applied on and/or over an X-ray detector and the peripheral edges of the polymeric substrate and peripheral edges of the metal barrier. In other embodiments, a metal barrier may be applied to the bottom of the polymeric substrate and peripheral edges or peripheral portion of the polymeric substrate, and then a sealing layer applied over an X-ray detector. Instead of employing a sealing layer, an X-ray detector disposed on a polymeric substrate having a metal barrier disposed on a bottom surface of the polymeric substrate as described above may be disposed in a sealed housing. In other embodiments, a sealing layer may be a metal lip-cover or can, a composite lip-cover or can, or include a glass sheet, which may be joined to a polymer substrate by edge encapsulation. The sealing layer such as a polymer sealant, a metal lip-cover or can, a composite lip-cover or can, or a glass sheet may be or may not be in contact with a scintillator, an organic photodiode, and/or a TFT array.

Figure 11:
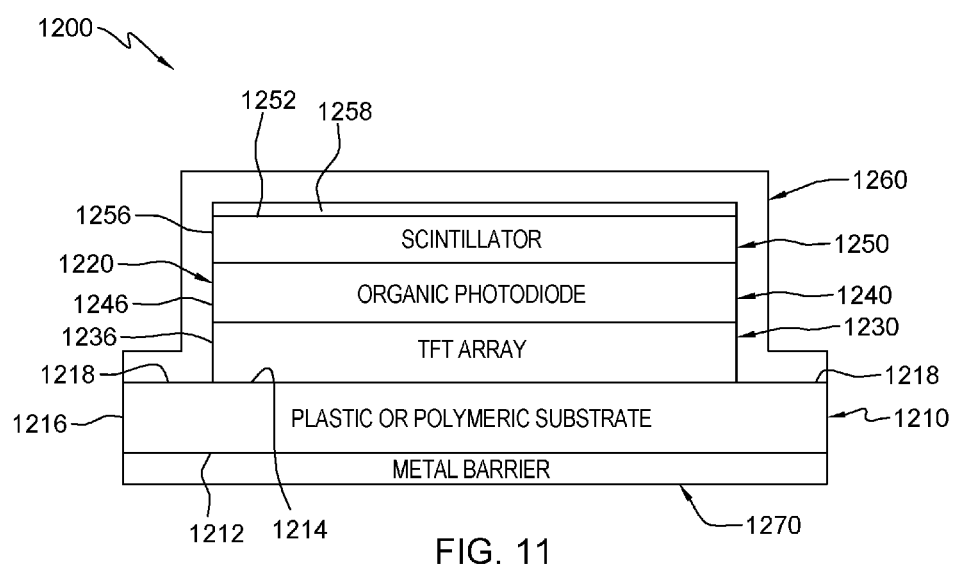
FIG. 11 is a cross-sectional view of another embodiment of an X-ray detector assembly in accordance with aspects of the present disclosure.

FIG. 11 illustrates another embodiment of an X-ray detector assembly 1200 in accordance with aspects of the present disclosure. In this illustrated embodiment, X-ray detector assembly 1200 may employ a metal material or metal barrier 1270 and a sealing layer 1260 that substantially surrounds an X-ray detector 1220. For example, X-ray detector assembly 1200 may include a plastic or polymeric substrate 1210, X-ray detector 1220 having, for example, a TFT (thin-film-transistor) array 1230 disposed on the polymeric substrate 1210, an organic photodiode 1240 disposed on the TFT array 1230, a scintillator 1250 disposed on the organic photodiode 1240, and metal barrier 1270 such as a metal coating disposed on a portion of polymeric substrate 1210.

Polymeric substrate 1210 may include a lower surface 1212, an upper surface 1214, and a peripherally-extending edge 1216. TFT array 1230 may be disposed on the upper surface 1214 of the polymeric substrate 1210. TFT array 1230 may include a peripherally-extending edge 1236, organic photodiode 1240 may include a peripherally-extending edge 1246, and scintillator 1250 may include a peripherally-extending edge 1256.

Metal barrier 1270 may extend substantially over lower surface 1212 of polymeric substrate 1210. In some embodiments, the metal barrier 1270 may be a continuous one-piece or monolithic metal barrier disposed entirely on the lower surface 1212 of polymeric substrate 1210.

Sealing layer 1260 may extend over X-ray detector 1220. In this illustrated embodiment, sealing layer 1260 may be extend over an upper surface 1252 and peripherally-extending edge 1256 of scintillator 1250, peripherally-extending edge 1246 of organic photodiode 1240, and peripherally-extending edge 1236 of TFT array 1230. A reflective layer 1258 may be disposed between scintillator 1250 and sealing layer 1260. The lower surface of the reflective layer aids in reflecting light downwardly towards the organic photodiode 1240 for increasing the absorption of light by the organic photodiode 1240. Sealing layer 1260 may be a polymer sealant such as an epoxy sealant, or other suitable sealing material.

It will be appreciated that in X-ray detectors where the peripherally-extending edges of the TFT array 1230, organic photodiode 1240, and scintillator 1250 do not align with each other, sealing layer 1260 may extend over peripherally-extending portions of the lower and/or upper surfaces of the TFT array 1230, organic photodiode 1240, and/or scintillator 1250. As shown in FIG. 11, polymeric substrate 1210 may include a peripherally extending portion which extends past the peripherally-extending edges of TFT array 1230. For example, in this illustrated embodiment, peripherally-extending edge portions of the polymer substrate 1210 may be sandwiched between the peripheral-extending edge portions of metal barrier 1270 and sealing layer 1260.

Metal barrier 1270 may provide a seal substantially extending below X-ray detector 1220 and on the bottom of polymeric substrate 1210. In this illustrated embodiment, metal barrier 1270 may extend substantially over the lower surface 1212 of polymeric substrate 1210. Metal barrier 1270 may provide a generally hermetic or airtight seal along the bottom of X-ray detector 1220 and lower surface 1212 of polymeric substrate 1210 that acts as a barrier to prevent the exposure of polymeric substrate 1210 to moisture, oxygen, and/or other gases. Metal barrier 1270 may also act as a barrier to chemical attack of the X-ray detector 1220 and polymeric substrate 1210. Suitable methods for applying the metal barriers or coatings may include, but not limited to, physical vapor deposition (PVD), thermal evaporation, sputtering, eBeam, etc.

As shown in FIG. 11, sealing layer 1260 may be applied onto X-ray detector and peripheral portions of polymer substrate 1210, and then metal barrier 1270 may be applied to the bottom of the polymeric substrate. In other embodiments, a metal barrier may be applied to the bottom of the polymeric substrate, and then a sealing layer or structure applied over an X-ray detector and the peripheral edges of the polymeric substrate and peripheral edges of the metal coating. In other embodiments, a metal barrier may be applied to the bottom of the polymeric substrate and peripheral edges or peripheral portion of the polymeric substrate, and then a sealing layer applied over an X-ray detector. Instead of employing a sealing layer, an X-ray detector disposed on a polymeric substrate having a metal barrier disposed on a bottom surface of the polymeric substrate may be disposed in a sealed housing. In other embodiments, a sealing layer may be a metal lip-cover or can, a composite lip-cover or can, or include a glass sheet which may be joined to a polymer substrate by edge encapsulation. The sealing layer such as a polymer sealant, a metal lip-cover or can, a composite lip-cover or can, or a glass sheet may be or may not be in contact with a scintillator, an organic photodiode, and/or a TFT array.

Figure 12:
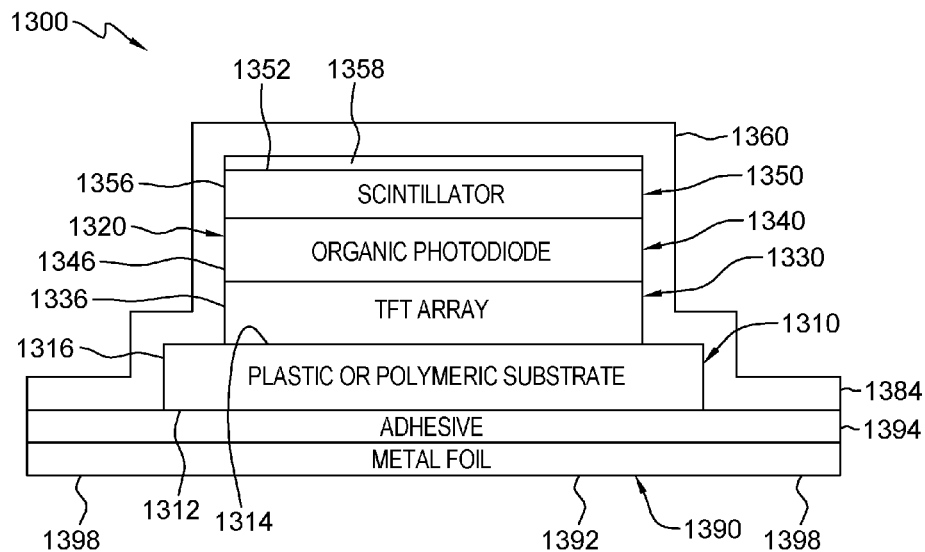
FIG. 12 is a cross-sectional view of another embodiment of an X-ray detector assembly in accordance with aspects of the present disclosure.

FIG. 12 illustrates another embodiment of an X-ray detector assembly 1300 in accordance with aspects of the present disclosure. In this illustrated embodiment, X-ray detector system 1300 may employ a metal barrier and a sealing layer 1360 that substantially surrounds an X-ray detector 1320. For example, X-ray detector assembly 1300 may include a plastic or polymeric substrate 1310, X-ray detector 1320 having, for example, a TFT (thin-film-transistor) array 1330 disposed on the polymeric substrate 1310, an organic photodiode 1340 disposed on the TFT array 1330, a scintillator 1350 disposed on the organic photodiode 1340, a metal barrier such as adhesively-backed metal foil 1390 disposed substantially on polymeric substrate 1310, and sealing layer 1360. For example, adhesively-backed metal foil 1390 may include metal foil 1392 having attached to one side of the metal foil adhesive layer 1394.

In this illustrated embodiment, polymeric substrate 1321 may include a lower surface 1312, an upper surface 1314, and a peripherally-extending edge 1316. TFT array 1330 may be disposed on the upper surface 1314 of the polymeric substrate 1310. TFT array 1330 may include a peripherally-extending edge 1336, organic photodiode 1340 may include a peripherally-extending edge 1346, and scintillator 1350 may include a peripherally-extending edge 1356. The adhesively-backed metal foil may be disposed on and removable from a roll. Alternatively, the adhesively-backed metal foil may be disposed in a sheet form having a releasably attached release sheet (not shown) for protecting the adhesive layer until removal of the release sheet. In still other embodiment, a spray of adhesive may be applied to a surface of the metal foil.

Adhesively-backed metal foil 1390 may extend substantially over lower surface 1312 of polymeric substrate 1310. In some embodiments, the adhesively-backed metal foil 1390 may be a continuous one-piece or monolithic adhesively-backed metal foil 1390 disposed entirely on the lower surface 1312 of polymeric substrate 1310.

Sealing layer 1360 may extend over X-ray detector 1320. In this illustrated embodiment, sealing layer 1360 may extend over upper surface 1352 and peripherally-extending edge 1356 of scintillator 1350, peripherally-extending edge 1346 of organic photodiode 1340, and peripherally-extending edge 1336 of TFT array 1330. A reflective layer 1358 may be disposed between scintillator 1350 and sealing layer 1360. The lower surface of the reflective layer 1358 aids in reflecting light downwardly towards the organic photodiode 1340 for increasing the absorption of light by the organic photodiode 1340. Sealing layer 1360 may be a polymer sealant such as an epoxy sealant, or other suitable sealing material.

A peripherally-extending portion 1398 of adhesively-backed metal foil 1390 may extend outwardly from the peripherally-extending side edge of the polymeric substrate 1310. Peripherally-extending portion of sealing layer 1360 may be attached to peripherally-extending portion of adhesive layer 1394.

In still other embodiments, an adhesive may be applied to the back of the metal foil or to the lower surface 1312 of the polymeric substrate 1310 prior to securing a metal foil. In other embodiments, a metal foil may be disposed on the lower surface 1312 of the polymeric substrate 1310, the X-ray detector 1320 fabricated on the upper surface 1314 of the polymeric substrate 1310, and then the sealing layer disposed over the X-ray detector 1320.

Metal foil 1390 and sealing layer 1360 may provide a seal substantially extending around X-ray detector 1320 and polymeric substrate 1310. In this illustrated embodiment, sealing layer 1360 may completely and continuously extend over an upper surface and side surfaces of X-ray detector 1320. Metal foil 1390 may extend over the lower surface 1312 of polymer substrate 1310. Metal foil 1390 may provide a generally hermetic or airtight seal along the bottom of lower surface 1312 of polymeric substrate 1310 that acts as a barrier to prevent the exposure of polymeric substrate 1310 to moisture, oxygen, and/or other gases. Metal foil 1390 may also act as a barrier to chemical attack of the X-ray detector 1320 and polymeric substrate 1310.

In other embodiments, an X-ray detector disposed on a polymeric substrate having a metal foil disposed on a bottom surface of the polymeric substrate such as shown in FIG. 12 may be disposed in a sealed housing. In other embodiments, such as shown in FIG. 12, a sealing layer may be a metal lip-cover or can, a composite lip-cover or can, or include a glass sheet which may be joined to a polymer substrate by edge encapsulation. The sealing layer such as a polymer sealant, a metal lip-cover or can, a composite lip-cover or can, or a glass sheet may be or may not be in contact with a scintillator, an organic photodiode, and/or a TFT array.

Figure 13:
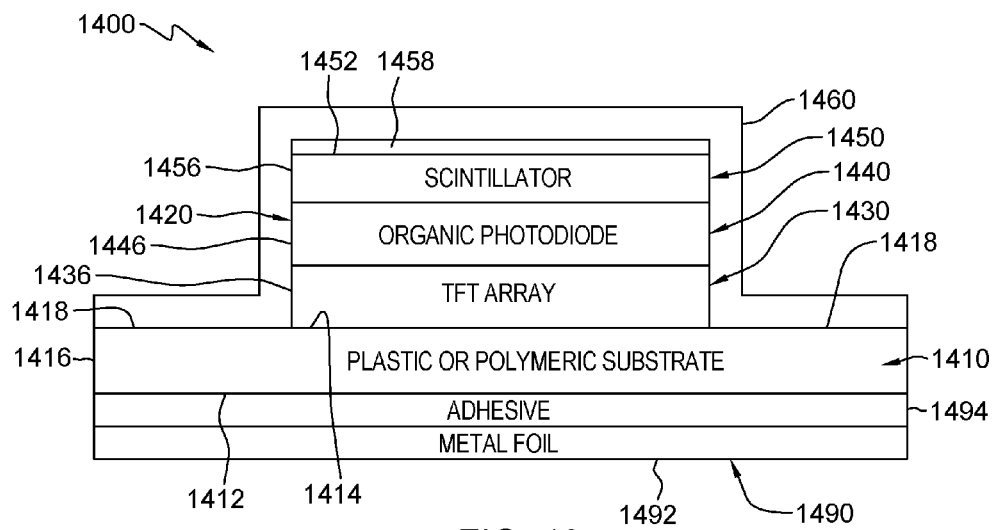
FIG. 13 is a cross-sectional view of another embodiment of an X-ray detector assembly in accordance with aspects of the present disclosure.

FIG. 13 illustrates another embodiment of an X-ray detector assembly 1400 in accordance with aspects of the present disclosure. In this illustrated embodiment, X-ray detector assembly 1400 may employ a metal barrier and a sealing layer 1460 that substantially surrounds an X-ray detector 1420. For example, X-ray detector assembly 1400 may include a plastic or polymeric substrate 1410, an X-ray detector 1420 having, for example, a TFT (thin-film-transistor) array 1430 disposed on the polymeric substrate, an organic photodiode 1440 disposed on the TFT array, a scintillator 1450 disposed on the organic photodiode, and a metal barrier such as an adhesively-backed metal foil 1490 disposed substantially on polymeric substrate 1410. For example, the adhesively-backed metal foil 1490 may include metal foil 1492 having attached to one side of the metal foil adhesive layer 1494.

In this illustrated embodiment, polymeric substrate 1420 may include a lower surface 1412, an upper surface 1414, and a peripherally-extending edge 1416. TFT array 1430 may be disposed on the upper surface of the polymeric substrate. TFT array 1430 may include a peripherally-extending edge 1436, organic photodiode 1440 may include a peripherally-extending edge 1446, and scintillator 1450 may include a peripherally-extending edge 1456. The adhesively-backed metal foil may be disposed on and removable from a roll. Alternatively, the adhesively-backed metal foil may be disposed in a sheet form having a releasably attached release sheet (not shown) for protecting the adhesive layer until removal of the release sheet. In still other embodiment, a spray of adhesive may be applied to a surface of the metal foil.

Adhesively-backed metal foil 1490 may extend substantially over lower surface 1412 of polymeric substrate 1410. In some embodiments, the adhesively-backed metal foil 1490 may be a continuous one-piece or monolithic adhesively-backed metal foil 1490 disposed entirely on the lower surface 1412 of polymeric substrate 1410.

Sealing layer 1460 may extend over X-ray detector 1420. In this illustrated embodiment, sealing layer 1460 may extend over upper surface 1452 and peripherally-extending edge 146 of scintillator 1350, peripherally-extending edge 1446 of organic photodiode 1440, and peripherally-extending edge 1436 of TFT array 1430. A reflective layer 1458 may be disposed between scintillator 1450 and adhesive layer 1484. The lower surface of the reflective layer aids in reflecting light downwardly towards the photodetector for increasing the absorption of light by the photodetector. Sealing layer 1460 may be a polymer sealant such as an epoxy sealant, or other suitable sealing material.

In still other embodiments, an adhesive may be applied to the back of the metal foil or to the lower surface of the substrate prior to securing the metal foil. In other embodiments, a metal foil may be disposed on the bottom surface of the substrate, the X-ray detectors fabricated on top of the substrate, and then the sealing layer disposed over the X-ray detector.

Metal foil 1490 and sealing layer 4160 may provide a seal substantially extending around X-ray detector 1420 and polymeric substrate 1410. Metal foil 1490 may provide a generally hermetic or airtight seal along the lower surface of polymeric substrate 1410 that acts as a barrier to prevent the exposure of the polymeric substrate to moisture, oxygen, and/or other gases. Metal foil 1490 may also act as a barrier to chemical attack of the X-ray detector and polymeric substrate.

In other embodiments, an X-ray detector disposed on a polymeric substrate having a metal foil disposed on a bottom surface of the polymeric substrate such as shown in FIG. 13 may be disposed in a sealed housing. In other embodiments, such as shown in FIG. 13, a sealing layer may be a metal lip-cover or can, a composite lip-cover or can, or include a glass sheet which may be joined to a polymer substrate by edge encapsulation. The sealing layer such as a polymer sealant, a metal lip-cover or can, a composite lip-cover or can, or a glass sheet may be or may not be in contact with a scintillator, an organic photodiode, and/or a TFT array.

Figure 14:
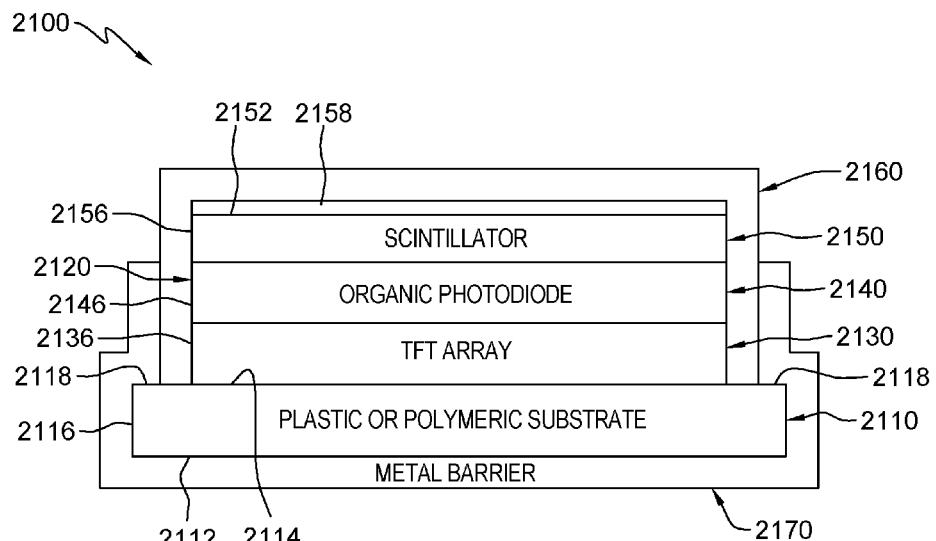
FIG. 14 is a cross-sectional view of another embodiment of an X-ray detector assembly in accordance with aspects of the present disclosure.

FIG. 14 illustrates an embodiment of an X-ray detector assembly 2100 in accordance with aspects of the present disclosure. In this illustrated embodiment, X-ray detector assembly 2100 may employ a metal barrier 2170 and a sealing layer 2160 that substantially surrounds an X-ray detector 2120. For example, X-ray detector assembly 2100 may include a plastic or polymeric substrate 2110, X-ray detector 2120 having, for example, a TFT (thin-film-transistor) array 2130 disposed on the polymeric substrate 2110, an organic photodiode 2140 disposed on the TFT array 2130, a scintillator 2150 disposed on the organic photodiode 2140, and metal barrier 2170 such as a metal coating disposed on a portion of polymeric substrate 2110 and around a portion of X-ray detector 2120.

Polymeric substrate 2110 may include a lower surface 2112, an upper surface 2114, and a peripherally-extending edge 2116. TFT array 2130 may be disposed on the upper surface 2114 of the polymeric substrate 2110. TFT array 2130 may include a peripherally-extending edge 2136, organic photodiode 2140 may include a peripherally-extending edge 2146, and scintillator 2150 may include a peripherally-extending edge 2156.

A sealing layer 2160 may extend over X-ray detector 2120. In this illustrated embodiment, sealing layer 2160 may extend over upper surface 2152 and peripherally-extending edge 2156 of scintillator 2150, peripherally-extending edge 2146 of organic photodiode 2140, and peripherally-extending edge 2136 of TFT array 2130. The sealing layer 2160 may electrically insulate metal barrier 2170 from the components of the X-ray detector 2120. A reflective layer 2158 may be disposed between scintillator 2150 and sealing layer 2160. The lower surface of the reflective layer 2158 aids in reflecting light downwardly towards the organic photodiode 2140 for increasing the absorption of light by the organic photodiode 2140. Sealing layer 2160 may be a polymer sealant such as an epoxy sealant, or other suitable sealing material.

Metal barrier 2170 may extend substantially over a peripherally-extending edge 2146 of organic photodiode 2140, peripherally-extending edge 2136 of TFT array 2130, a peripherally-extending edge 2116 of polymeric substrate 2110, and lower surface 2112 of polymeric substrate 2110. In some embodiments, the metal barrier 2170 may be a continuous one-piece or monolithic metal barrier disposed entirely around the lower surface 2112 of polymeric substrate 2110, peripherally-extending edge 2116 of polymeric substrate 2110, peripherally-extending edge 2136 of TFT array 2130, and peripherally-extending edge 2146 of organic photodiode 2140.

It will be appreciated that in X-ray detectors where the peripherally-extending edges of the TFT array 2130, organic photodiode 2140, and scintillator 2150 do not align with each other, the metal barrier 2170 and the sealing layer 2160 may extend over peripherally-extending portions of the lower and/or upper surfaces of the TFT array 2130, organic photodiode 2140, and/or scintillator 2150. For example, as shown in FIG. 14, polymeric substrate 2110 may include a peripherally extending upper edge portion 2118 which extends past the peripherally-extending edges 2136 of TFT array 2130. Metal barrier 2170 may extend over a peripherally-extending upper edge portion 2118 of polymer substrate 2110.

As described above, metal barrier 2170 may provide a seal substantially extending below X-ray detector 2120 and along portions of the sides of X-ray detector 2120. In this illustrated embodiment, metal barrier 2170 may completely and continuously extend along the bottom of polymeric substrate 2110 and around the sides of X-ray detector 2120.

Metal barrier 2170 may provide a generally hermetic or airtight seal or closure around the bottom of polymeric substrate 2110 and a portion of X-ray detector 2120 that acts as a barrier to prevent the exposure of polymeric substrate 2110 and X-ray detector 2120 to moisture, oxygen, and/or other gases. Metal barrier 2170 may also act as a barrier to chemical attack of the X-ray detector 2120 and polymeric substrate 2110. Suitable methods for applying the metal barrier 2170 or coating may include, but not limited to, physical vapor deposition (PVD), thermal evaporation, sputtering, eBeam, etc.

As shown in FIG. 14, sealing layer 2160 may be applied onto X-ray detector 2120 and upper surfaces of polymer substrate 2110, and then metal barrier 2170 may be applied to bottom surface 2112 of polymeric substrate 2110, peripheral edge 2116 of polymeric substrate 2110, and lower portion of sealing layer 2160.

Figure 15:
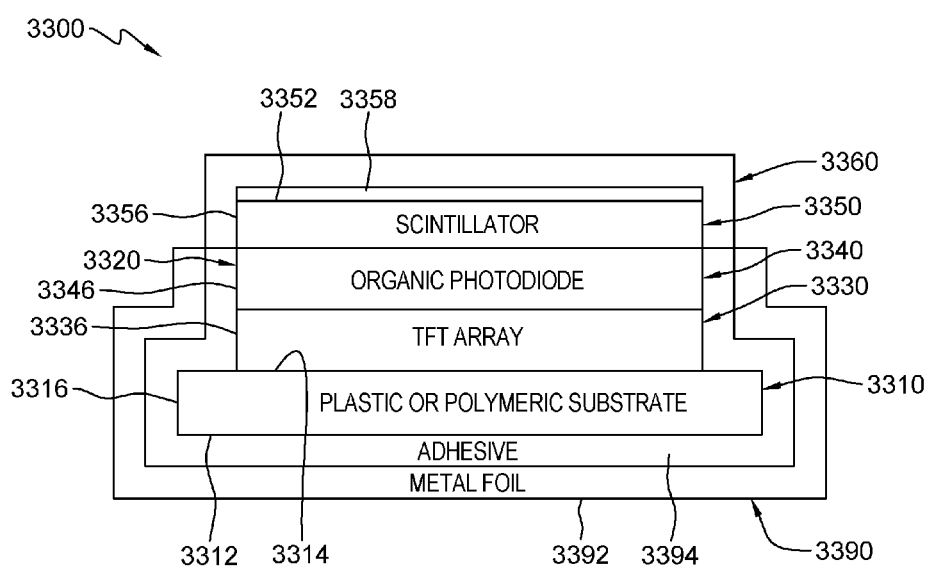
FIG. 15 is a cross-sectional view of another embodiment of an X-ray detector assembly in accordance with aspects of the present disclosure.

FIG. 15 illustrates another embodiment of an X-ray detector assembly 3300 in accordance with aspects of the present disclosure. In this illustrated embodiment, X-ray detector system 3300 may employ a metal barrier and a sealing layer that substantially surrounds an X-ray detector 1320. For example, X-ray detector assembly 3300 may include a plastic or polymeric substrate 3310, X-ray detector 3320 having, for example, a TFT (thin-film-transistor) array 3330 disposed on the polymeric substrate 3310, an organic photodiode 3340 disposed on the TFT array 3330, a scintillator 3350 disposed on the organic photodiode 3340, a metal barrier such as adhesively-backed metal foil 3390 disposed around a portion of X-ray detector 3320 supported on polymeric substrate 3310, and a sealing layer 3360. For example, adhesively-backed metal foil 3390 may include metal foil 3392 having attached to one side of the metal foil adhesive layer 3394.

In this illustrated embodiment, polymeric substrate 3310 may include a lower surface 3312, an upper surface 3314, and a peripherally-extending edge 3316. TFT array 3330 may be disposed on the upper surface 3314 of the polymeric substrate 3310. TFT array 3330 may include a peripherally-extending edge 3336, organic photodiode 3340 may include a peripherally-extending edge 3346, and scintillator 3350 may include a peripherally-extending edge 3356. The adhesively-backed metal foil may be disposed on and removable from a roll. Alternatively, the adhesively-backed metal foil may be disposed in a sheet form having a releasably attached release sheet (not shown) for protecting the adhesive layer until removal of the release sheet. In still other embodiment, a spray of adhesive may be applied to a surface of the metal foil. The adhesive layer may act as an insulating layer that extends between the metal foil 3392 and X-ray detector 3320 to electrically insulate the metal foil from the components of the X-ray detector 3320.

Adhesively-backed metal foil 3390 may extend substantially over lower surface 3312 and upper surface 3314 of polymeric substrate 3310. In some embodiments, the adhesively-backed metal foil 3390 may be a continuous one-piece or monolithic adhesively-backed metal foil 3390 disposed entirely on the lower surface 3312 and around polymeric substrate 3310.

Sealing layer 3360 may extend over X-ray detector 3320. In this illustrated embodiment, sealing layer 3360 may extend over upper surface 3352 and peripherally-extending edge 3356 of scintillator 3350. A reflective layer 3358 may be disposed between scintillator 3350 and sealing layer 3360. The lower surface of the reflective layer 3358 aids in reflecting light downwardly towards the organic photodiode 3340 for increasing the absorption of light by the organic photodiode 3340. Sealing layer 2160 may be a polymer sealant such as an epoxy sealant, or other suitable sealing material. Sealing layer 2160 may be, or other suitable sealing material.

In this illustrated embodiment shown in FIG. 15, adhesively-backed metal foil 3390 may be wrapped substantially over the lower portion of X-ray detector 3320. In still other embodiments, an adhesive may be applied to the back of the metal foil or to portions of the outer surfaces of the X-ray detector 3320 and lower surface 3312 of the polymeric substrate 3310 prior to securing the metal foil.

Metal foil 3390 and sealing layer 3360 may provide a seal substantially extending around X-ray detector 3320 and polymeric substrate 3310. In this illustrated embodiment, sealing layer 3360 may completely and continuously extend over an upper surface and side surfaces of scintillator 3350. Metal foil 3390 may provide a generally hermetic or airtight seal or closure around lower portion of polymeric substrate 3310, peripheral edges 3316 of polymeric substrate 3310, and peripheral edges 3336 of TFT array 3330, and peripheral edge 3346 of organic photodiode 3340 that acts as a barrier to prevent the exposure of the X-ray detector 3320 and polymeric substrate 3310 to moisture, oxygen, and/or other gases. Metal foil 3390 may also act as a barrier to chemical attack of the X-ray detector 3320 and polymeric substrate 3310.

Figure 16:
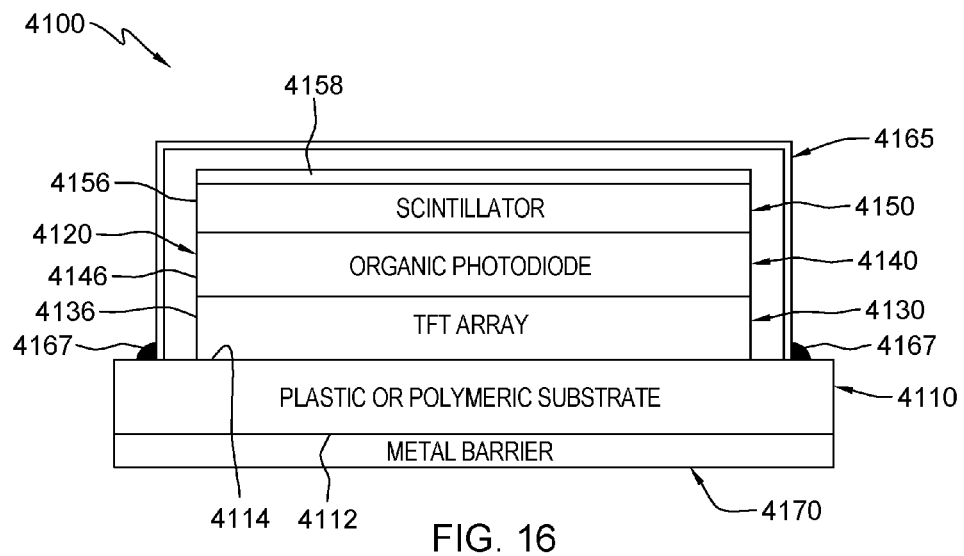
FIG. 16 is a cross-sectional view of another embodiment of an X-ray detector assembly in accordance with aspects of the present disclosure.

FIG. 16 illustrates another embodiment of an X-ray detector assembly 4100 in accordance with aspects of the present disclosure. In this illustrated embodiment, X-ray detector system 4100 may employ a metal barrier 4170 and a sealing layer 4165 that substantially surrounds an X-ray detector 4120. For example, X-ray detector assembly 4100 may include a plastic or polymeric substrate 4110, X-ray detector 4120 having, for example, a TFT (thin-film-transistor) array 4130 disposed on the polymeric substrate 4110, an organic photodiode 4140 disposed on the TFT array 4130, a scintillator 4150 disposed on the organic photodiode 4140, metal barrier 4170 such a metal coating, a metal foil, or an adhesively-backed metal foil as described above disposed on polymeric substrate 4110, and sealing layer 4165 such as a lip-cover or can. A lower portion sealing layer 4165 or lip-cover or can may be joined, edge encapsulated, or sealed to an upper surface 4114 of polymeric substrate 4110 such as with a sealer 4167. Sealer 4167 may be a polymer sealant such as an epoxy sealant, or other suitable sealing material. Sealing layer 4165 may be a metal lip-cover or can or a composite lip-cover or can. The inside surfaces of lip-cover or can may be spaced from and not in contact with X-ray detector 4120. For example, the inside surfaces of lip-cover or can may be spaced from and not in contact with a reflective layer 4158, a peripherally-extending edge 4136 of TFT array 4130, a peripherally-extending edge 4146 of organic photodiode 4140, and a peripherally-extending edge 4156 of scintillator 4150. Metal barrier 4170 may provide a generally hermetic or airtight seal or closure around a lower surface 4112 of polymeric substrate 4110 that acts as a barrier to prevent the exposure of the X-ray detector 4120 and polymeric substrate 4110 to moisture, oxygen, and/or other gases. Metal barrier 4170 may also act as a barrier to chemical attack of the X-ray detector 4120 and polymeric substrate 4110.

Figure 17:
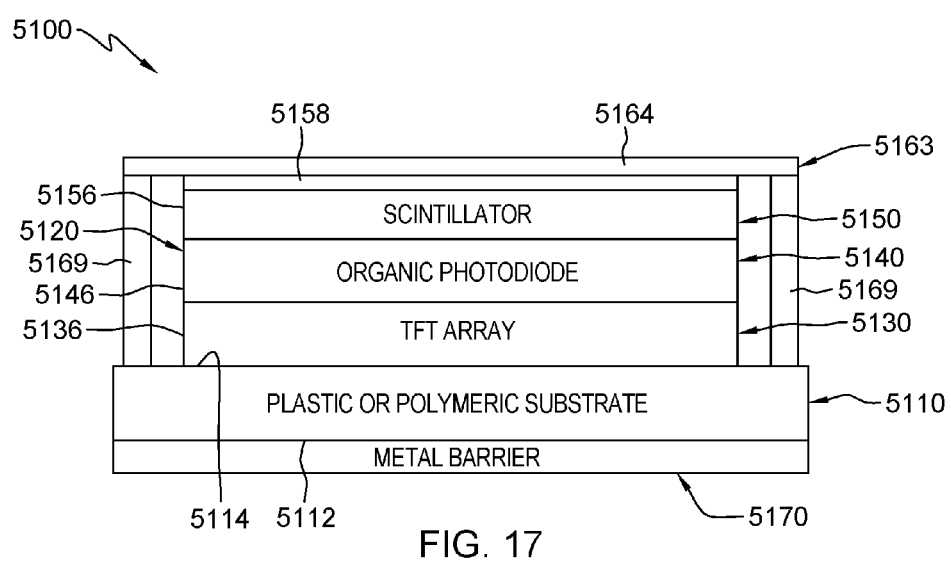
FIG. 17 is a cross-sectional view of another embodiment of an X-ray detector assembly in accordance with aspects of the present disclosure.

FIG. 17 illustrates another embodiment of an X-ray detector assembly 5100 in accordance with aspects of the present disclosure. In this illustrated embodiment, X-ray detector system 5100 may employ a metal barrier 5170 and sealing layer 5165 that substantially surrounds an X-ray detector 5120. For example, X-ray detector assembly 5100 may include a plastic or polymeric substrate 5110, X-ray detector 5120 having, for example, a TFT (thin-film-transistor) array 5130 disposed on the polymeric substrate 5110, an organic photodiode 5140 disposed on the TFT array 5130, a scintillator 5150 disposed on the organic photodiode 5140, metal barrier 5170 such a metal coating, a metal foil, or an adhesively-backed metal foil as described above disposed on polymeric substrate 5110, sealing layer 5163 such as a glass panel or sheet 5164 and a sealer 5169 for coupling a bottom surface of glass sheet 5164 to an upper surface 5114 of polymeric substrate 5110. Sealer 5169 may be a polymer sealant such as an epoxy sealant, or other suitable sealing material. The inside surfaces of sealer 5169 may be spaced from and not in contact with X-ray detector 5120. For example, the inside surfaces of sealer 5169 may be spaced from and not in contact with a reflective layer 5158, a peripherally-extending edge 5136 of TFT array 5130, a peripherally-extending edge 5146 of organic photodiode 5140, and a peripherally-extending edge 5156 of scintillator 5150. Metal barrier 5170 may provide a generally hermetic or airtight seal or closure around a lower surface 5112 of polymeric substrate 5110 that acts as a barrier to prevent the exposure of the X-ray detector 5120 and polymeric substrate 5110 to moisture, oxygen, and/or other gases. Metal barrier 5170 may also act as a barrier to chemical attack of the X-ray detector 5120 and polymeric substrate 5110.

With reference again to FIG. 5, FIG. 5 illustrates a block diagram of X-ray detector system 500 for imaging object 501 in accordance with aspects of the present disclosure. For example, X-ray detector system 500 may include an X-ray detector assembly 510, such as the techniques disclosed in X-ray detector assemblies 1100 (FIG. 10), 1200 (FIG. 11), 1300 (FIG. 12), 1400 (FIG. 13), 2100 (FIG. 14), 3300 (FIG. 15), 4100 (FIG. 16), and 5100 (FIG. 17), an X-ray source 520, and a computing unit 540.

With reference again to FIG. 6, FIG. 6 illustrates a block diagram of X-ray detector system 600 for imaging object 601 in accordance with aspects of the present disclosure. For example, X-ray detector system 600 may include an X-ray detector assembly 610, such as the techniques disclosed in X-ray detector assemblies 1100 (FIG. 10), 1200 (FIG. 11), 1300 (FIG. 12), 1400 (FIG. 13), 2100 (FIG. 14), 3300 (FIG. 15), 4100 (FIG. 16), and 5100 (FIG. 17), X-ray source 620, and computing unit 640.

With reference again to FIG. 7, FIG. 7 illustrates a block diagram of an X-ray detector system 700 for imaging an object 701 in accordance with aspects of the present disclosure. For example, X-ray detector system 700 may include an X-ray detector assembly 710, such as X-ray detector assembly employing the techniques disclosed in the X-ray detector assemblies 1100 (FIG. 10), 1200 (FIG. 11), 1300 (FIG. 12), 1400 (FIG. 13), 2100 (FIG. 14), 3300 (FIG. 15), 4100 (FIG. 16), and 5100 (FIG. 17), X-ray source 720, and computing unit 740.

Figure 18:
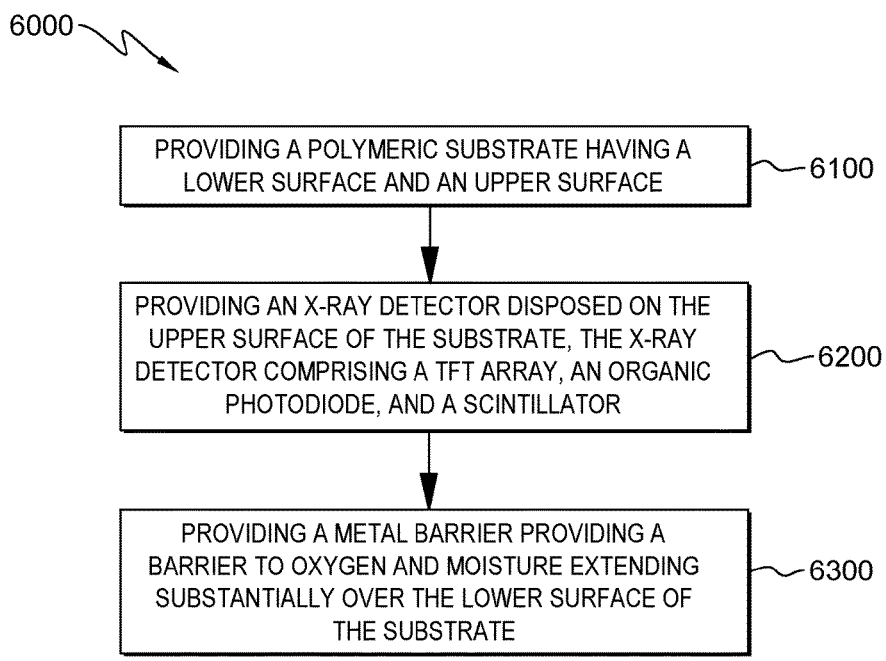
FIG. 18 is a flowchart of one embodiment of a method for forming an organic X-ray detector in accordance with aspects of the present disclosure.

FIG. 18 illustrates one embodiment of a method 6000 for fabricating an X-ray detector assembly. In this exemplary embodiment, method 6000 may include at 6100, providing a polymeric substrate having a lower surface and an upper surface, and at 6200, providing an X-ray detector disposed on the upper surface of the polymeric substrate. The X-ray detector includes a TFT (thin-film-transistor) array, an organic photodiode, and a scintillator. At 6300, a metal barrier is provided providing a barrier to oxygen and moisture extending substantially over the lower surface of the polymeric substrate.

In the various embodiments of the present disclosure, the metal barrier such as the metal coating or metal foil may include a suitable metal material. For example, the metal material may include aluminum, silver, copper, other suitable elemental metals, and/or combinations thereof. The metal barrier may be a solid metal such as a metal barrier composed of substantially entirely a specified metal material or materials, e.g., such as made substantially entirely from aluminum, silver, copper, other metals, and/or combinations thereof. For example, the metal barrier may be an opaque crystalline material, and may exhibit high strength, good electrical and thermal conductivities, ductility, and reflectivity. The metal barrier may be composed of a metal in elemental form, one or more metals or metal alloys, etc. The metal alloy or alloys may comprise metals in elemental form. Suitable materials for the metal barrier substantially does not include metal oxides. For example, a metal barrier may be substantially entirely a metal with, e.g., a thin, light, naturally occurring oxide coating formed on outer surfaces of the barrier metal. A suitable thickness for the metal barrier may range between about 100 nanometers to about 5 millimeters, about 1 micron to about 1 millimeter, or about 1 micron to about 100 microns. The metal barrier may have a constant thickness, or may have a varying thickness around the X-ray detector and substrate.

Suitable adhesive materials include epoxy, acrylate, thermoplastic, thermoset, polyurethane, pressure sensitive coatings and adhesives. Adhesive layer may further include moisture absorbing, oxygen absorbing, and/or additives that improve coating and moisture barrier properties.

In the above illustrated embodiments, the polymeric substrate may be composed of a rigid or flexible material. Examples of suitable materials for a polymeric substrate may include rigid or flexible, plastics such as polyethylene terephthalate, polybutylene phthalate, polyethylene naphthalate, polystyrene, polycarbonate, polyether sulfone, polyallylate, polyimide, polycycloolefin, norbornene resins, and fluoropolymers. Other suitable material for a substrate may include glass, which may be metals or metal foils such as stainless steel, aluminum, silver and gold, metal oxides, such as titanium oxide and zinc oxide, and semiconductors such as silicon. Combinations of materials may also be used. By using an unbreakable material instead of a fragile glass substrate for the X-ray detector, the components and materials designed to absorb bending stress or drop shock can be reduced in size and weight or eliminated, and the overall weight and thickness of the detector can be reduced. Removing costly materials which are used to protect the glass substrate decreases the overall cost of the detector. The substrate may have a flat form, curved form, and/or a flexible form. The substrate materials may further include additional functional layers such as a hard-coat, a chemical resistant coating, a planarization/smoothing layer, and other materials, and combinations thereof.

The TFT array may be a two dimensional array of passive or active pixels which store charge for read out by electronics, disposed on an active layer formed of amorphous silicon or an amorphous metal oxide, or organic semiconductors. Suitable amorphous metal oxides include zinc oxide (ZnO), zinc tin oxide, indium oxides, indium zinc oxides (In—Zn—O series), indium gallum oxides, gallium zinc oxides, indium silicon zinc oxides, and indium gallium zinc oxides (IGZO). IGZO materials include $InGaO_3(ZnO)_m$ where m is <6) and $InGaZnO_4$. Suitable organic semiconductors include, but are not limited to, conjugated aromatic materials, such as rubrene, tetracene, pentacene, perylenediimides, tetracyanoquinodimethane and polymeric materials such as polythiophenes, polybenzodithiophenes, polyfluorene, polydiacetylene, poly(2,5-thiophenylene vinylene) and poly(p-phenylene vinylene) and derivatives thereof. Each pixel contains a patterned second electrode 3.

The organic photodiode may include, but not limited to, an organic polymeric semiconductors or an organic compound semiconductors. The photodetector may be fabricated directly over the imaging TFT array. The photodetector 35 may include an anode, a cathode, and an organic film between the anode and cathode which produces charged carriers in response to absorption of light.

The scintillator may be composed of a phosphor material that is capable of converting X-rays to visible light. The wavelength region of light emitted by the scintillator may range from about 360 nm to about 830 nm. Suitable materials for the scintillator include, but are not limited to, organic scintillators, cesium iodide (CsI), CsI (TI) (cesium iodide to which thallium has been added) and terbium-activated gadolinium oxysulfide (GOS), LuOx, BGO, etc. Such materials are commercially available in the form of a sheet or screen. Other suitable forms of the scintillator include a direct-deposited scintillator coating or may be deposited via a particle-in-binder. Prior to applying and sealing the metal barrier, an inert gas such as nitrogen (N₂) or argon (Ar) may be introduced to remove ambient air from the X-ray detector.

It is to be understood that the above description is intended to be illustrative, and not restrictive. Numerous changes and modifications may be made herein by one of ordinary skill in the art without departing from the general spirit and scope of the disclosure as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably" in conjunction with terms such as coupled, connected, joined, sealed or the like is used herein to refer to both connections resulting from separate, distinct components being directly or indirectly coupled and components being integrally formed (i.e., one-piece, integral or monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the disclosure. Additionally, while various embodiments have been described, it is to be understood that aspects of the disclosure may include only some of the described embodiments. Accordingly, the disclosure is not to be seen as limited by the foregoing description, but is only limited by the scope of the appended claims.

This written description uses examples, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. An X-ray detector assembly comprising:
   a polymeric substrate having a lower surface and an upper surface;
   an X-ray detector disposed on said upper surface of said polymeric substrate, said X-ray detector comprising:
      a thin-film-transistor array disposed on said polymeric substrate;
      an organic photodiode disposed on said thin-film-transistor array; and
      a scintillator disposed on said organic photodiode;
   a metal barrier extending substantially over said lower surface of said polymeric substrate;
   wherein said metal barrier extends continuously over an entire lower surface of said polymeric substrate, peripherally-extending edges of said polymeric substrate, and peripherally extending upper edge portion of said polymeric substrate.

2. The X-ray detector assembly of claim 1, wherein said metal barrier extends over said organic photodiode, and said thin-film-transistor array.

3. The X-ray detector assembly of claim 1, wherein said metal barrier comprises a metal coating.

4. The X-ray detector assembly of claim 1, wherein said metal barrier comprises a metal foil.

5. The X-ray detector assembly of claim 1, wherein said metal barrier comprises a metal foil and an adhesive layer.

6. The X-ray detector assembly of claim 5, wherein said metal foil extends over edges of said polymeric substrate.

7. The X-ray detector assembly of claim 6, wherein said metal foil extends over edges of said polymeric substrate, said organic photodiode, and said thin-film-transistor array.

8. The X-ray detector assembly of claim 1, wherein said metal barrier comprises a thickness of at least 1 micrometer to 1 millimeter.

9. The X-ray detector assembly of claim 1, further comprising a sealing layer disposed over a top surface of said scintillator and over edges of said scintillator.

10. The X-ray detector assembly of claim 1, further comprising a sealing layer disposed over a top surface of said scintillator, and over side edges of said scintillator, said organic photodiode, and said thin-film-transistor array.

11. The X-ray detector assembly of claim 1, wherein said metal barrier comprises aluminum, silver, copper, and/or combinations thereof.

12. The X-ray detector assembly of claim 1, wherein said X-ray detector is flexible.

13. An X-ray system comprising:
   said X-ray detector assembly of claim 1;
   an X-ray source; and
   a controller operable for controlling said X-ray source and said X-ray detector assembly.

14. An X-ray system comprising:
   said X-ray detector assembly of claim 6;
   an X-ray source; and
   a controller operable for controlling said X-ray source and said X-ray detector assembly.

* * * * *